US012655387B2

(12) United States Patent
Fukuda et al.

(10) Patent No.: US 12,655,387 B2
(45) Date of Patent: Jun. 16, 2026

(54) HAIR FOLLICLE PRIMORDIA AND METHOD FOR PRODUCING SAME

(71) Applicants:National University Corporation Yokohama National University, Kanagawa (JP); Kanagawa Institute of Industrial Science and Technology, Kanagawa (JP)

(72) Inventors: Junji Fukuda, Yokohama (JP); Tatsuto Kageyama, Ebina (JP); Akihiro Shimizu, Yokohama (JP); Rikuma Nakajima, Yokohama (JP); Riki Anakama, Yokohama (JP)

(73) Assignees: National University Corporation Yokohama National University, Kanagawa (JP); Kanagawa Institute of Industrial Science and Technology, Kanagawa (JP)

( * ) Notice: Subject to any disclaimer, the term of this patent is extended or adjusted under 35 U.S.C. 154(b) by 635 days.

(21) Appl. No.: 17/609,164

(22) PCT Filed: Aug. 7, 2019

(86) PCT No.: PCT/JP2019/031142
§ 371 (c)(1),
(2) Date: Nov. 5, 2021

(87) PCT Pub. No.: WO2020/225934
PCT Pub. Date: Nov. 12, 2020

(65) Prior Publication Data
US 2022/0228113 A1      Jul. 21, 2022

(30) Foreign Application Priority Data
May 7, 2019     (JP) ................................. 2019-087747

(51) Int. Cl.
*C12N 5/071*            (2010.01)
(52) U.S. Cl.
CPC ...... *C12N 5/0628* (2013.01); *C12N 2502/092* (2013.01); *C12N 2502/1388* (2013.01); *C12N 2513/00* (2013.01); *C12N 2533/54* (2013.01)
(58) Field of Classification Search
None
See application file for complete search history.

(56) References Cited

U.S. PATENT DOCUMENTS

| | | | |
|---|---|---|---|
| 8,980,628 | B2 | 3/2015 | Qiao et al. |
| 2016/0184481 | A1 | 6/2016 | Thangapazham et al. |
| 2018/0355315 | A1 | 12/2018 | Tsuji et al. |
| 2019/0062687 | A1 | 2/2019 | Fukuda et al. |
| 2020/0208106 | A1 | 7/2020 | Fukuda et al. |

FOREIGN PATENT DOCUMENTS

| | | | | |
|---|---|---|---|---|
| CN | 108138133 | A | 6/2018 | |
| JP | 2018-82638 | A | 5/2018 | |
| WO | WO-2009118283 | A1 * | 10/2009 | ......... A61L 27/3604 |
| WO | 2014/179559 | A1 | 11/2014 | |
| WO | 2016/039279 | A1 | 3/2016 | |
| WO | 2017/073625 | A1 | 5/2017 | |
| WO | 2019/039376 | A1 | 2/2019 | |

OTHER PUBLICATIONS

Corning® Matrigel® Matrix, Frequently Asked Questions, 8 pages, retrieved from the internet (Jun. 26, 2024): file:///C:/Users/epyla/Documents/17%20Series%20Applications/17609164/Corning%C2%AE%20Matrigel%C2%AE%20Matrix%20%20laminin%20entactin%20collagen%204.pdf (Year: 2024).*
Danysh et al., Experimental Eye Research 88 (2009) 151-164 (Year: 2009).*
Marionnet et al., Journal of Investigative Dermatology (2006), vol. 126, pp. 971-979 (Year: 2006).*
Tobin et al., Journal of Investigative Dermatology (1995), vol. 104, No. 1, pp. 86-89 (Year: 1995).*
Funaki et al., "Technologies to Engineer Cell Substrate Mechanics in Hydrogels," Biology and Engineering of Stem Cell Niches, <<https://www.sciencedirect.com/topics/medicine-and-dentistry/matrigel>> (2017).
Extended European Search Report issued in corresponding European Patent Application No. 19927959.7 dated Apr. 5, 2023.
Kageyama et al. "Spontaneous hair follicle germ (HFG) formation in vitro, enabling the large-scale production of HFGs for regenerative medicine," Biomaterials, 154: 291-300 (2018).
Miyakura et al. "The influence of extracellular matrix and growth factors on early hair follicle development using hair batch assay," The Journal of Tokyo Medical University, 69 (2): 210-218 (2011).
Anonymous, "Matrigel—an overview", Jan. 1, 2018, <<https://www.sciencedirect.com/topics/medicine-and-dentistry/matrigel>> [retrieved from the internet on Mar. 28, 2023].
Sugawara et al. "Laminin-332 and -511 in skin," Experimental Dermatology, 17 (6): 473-480 (2008).
Kageyama et al. "Reprogramming of three-dimensional microenvironments for in vitro hair follicle induction," Science Advances, 8 (42): eadd4603 (2022).
Kageyama et al. "Preparation of hair beads and hair follicle germs for regenerative medicine," Biomaterials, 212: 55-63 (2019).
Office Action dated Feb. 26, 2024, issued in corresponding European Patent Application No. 19927959.7.
Kageyama et. al. "In vitro hair follicle growth model for drug testing", Scientific Reports, 13:1, (2023), XP93133483.
Office Action dated Oct. 14, 2024 issued in corresponding European Patent Application No. 19927959.7.

(Continued)

*Primary Examiner* — Evelyn Y Pyla
(74) *Attorney, Agent, or Firm* — Morgan, Lewis & Bockius LLP

(57) ABSTRACT

Provided is a hair follicle germ capable of forming a hair shaft-like structure in vitro simply and within a short period of time. A method of producing a hair follicle germ includes: inoculating epithelial cells and mesenchymal cells; maintaining the epithelial cells and the mesenchymal cells in a culture solution in which (a) laminin and entactin, and/or (b) type IV collagen is dispersed; and co-culturing the epithelial cells and the mesenchymal cells in a culture solution to form a hair follicle germ.

19 Claims, 36 Drawing Sheets

(56)                    References Cited

OTHER PUBLICATIONS

Shimizu et al. "P-40: Fabrication of hairfollicle model in vitro by long-term culture ofhair follicle germs", AATEX—Alternativesto Animal Testing Andexperimentation; Abstracts of THE31ST Annual Meeting of the JSAAE, Aatex. 2018; Nov. 23 to 25, 2018,Japanese Society for Alternativeto Animal Experiments, JP,vol. 23(Supplement), Dec. 31, 2018,pp. 129, XP009549353.

Thibaut et al. "Human hair shape isprogrammed from the bulb", Britishjournal of Dermatology (1951), Wiley, vol. 152, No. 4, Mar. 24, 2005,pp. 632-638, XP071053395.

Ouji et al. Promotion of hair follicledevelopment and trichogenesis by Wnt-10bin cultured embryonic skin and inreconstituted skin, Biochemical Andbiophysical Researchcommunications, Elsevier, Amsterdam, NL, vol. 345, No. 2, Jun. 30, 2006, pp. 581-587, XP005455394.

Lee et al., "Hair follicle development in mouse pluripotent stem cell-derived skin organoids," Cell Reports, 22: 242-254 (2018) (experimental procedures).

Corning Matrigel Basement Membrane Matrix, Corning International KK Life Sciences Business Segment 1-31, p. 3 (2016) (see International Search Report).

International Search Report issued in corresponding International Patent Application No. PCT/JP2019/031142 dated Nov. 5, 2019.

* cited by examiner

Laminin

Laminin/Entactin

CollagenIV

HAIR FOLLICLE PRIMORDIA AND METHOD FOR PRODUCING SAME

TECHNICAL FIELD

The present invention relates to a hair follicle germ and a method of producing the same.

BACKGROUND ART

In Non-Patent Literature 1, there is a description that induced pluripotent stem cells (iPSCs) generated from mouse embryonic fibroblasts are inoculated in a 96-well plate and cultured to form skin organoids in vitro.

In Patent Literature 1, there is a description of a regenerated hair follicle germ aggregation manufacturing method, including a step of forming hair follicle germs by inoculating a microwell plate, which includes regularly arranged microwell portions, with mesenchymal cells and epithelial cells and culturing a mixture of the cells while supplying oxygen thereto.

In Patent Literature 2, there is a description of a method for manufacturing full-thickness skin with skin appendage, characterized in that the "full-thickness skin with skin appendage" includes at least the following (1)-(3): (1) skin including epidermal and dermal layers, (2) at least one type of skin appendage, and (3) subcutaneous tissue, wherein the method includes the following steps: (a) a step of stimulating an embryoid body with a bioactive substance that may activate the Wnt pathway; (b) a step of preparing a conjugate including the following (A) and (B): (A) all or a part of the embryoid body stimulated in step (a) and (B) a scaffolding material; (c) a step of transplanting the conjugate prepared in the step (b) to an animal; and (d) a step of manufacturing full-thickness skin derived from the conjugate in the animal.

CITATION LIST

Patent Literature

[PTL 1] WO 2017/073625 A1
[PTL 2] WO 2016/039279 A1

Non-Patent Literature

[NPL 1] Jiyoon Lee et al. (2018). Hair Follicle Development in Mouse Pluripotent Stem Cell-Derived Skin Organoids. Cell Reports 22, 242-254

SUMMARY OF INVENTION

Technical Problem

However, the method described in Non-Patent Literature 1 involves complicated operations and requires a relatively long culture period owing to the use of induced pluripotent stem cells.

The present invention has been made in view of the above-mentioned problem, and one of the objects of the present invention is to provide a hair follicle germ capable of forming a hair shaft-like structure in vitro simply and within a short period of time.

Solution to Problem

In order to solve the above-mentioned problem, according to one embodiment of the present invention, in one aspect, there is provided a method of producing a hair follicle germ, including: inoculating epithelial cells and mesenchymal cells; maintaining the epithelial cells and the mesenchymal cells in a culture solution in which (a) laminin and entactin, and/or (b) type IV collagen is dispersed; and co-culturing the epithelial cells and the mesenchymal cells in a culture solution to form a hair follicle germ. According to the one embodiment of the present invention, there is provided a method of producing a hair follicle germ capable of forming a hair shaft-like structure in vitro simply and within a short period of time.

The above-mentioned method may include maintaining the epithelial cells and the mesenchymal cells in a culture solution in which the (a) laminin and entactin are dispersed. The above-mentioned method may include maintaining the epithelial cells and the mesenchymal cells in a culture solution in which the (b) type IV collagen is dispersed.

The above-mentioned method may further include causing the inoculated epithelial cells and mesenchymal cells to be sedimented on a culture substrate in a culture solution, wherein the method includes maintaining the epithelial cells and the mesenchymal cells sedimented on the culture substrate in the culture solution in which the (a) and/or the (b) is dispersed. The above-mentioned method may include, after maintaining the epithelial cells and the mesenchymal cells in the culture solution in which the (a) and/or the (b) is dispersed, co-culturing the epithelial cells and the mesenchymal cells in a culture solution in which a concentration of the (a) and/or the (b) is lower than that in the solution in which the epithelial cells and the mesenchymal cells were maintained. The above-mentioned method may include forming the hair follicle germ having a hair shaft-like structure by the co-culture.

In order to solve the above-mentioned problem, according to one embodiment of the present invention, in another aspect, there is provided a method of promoting formation of a hair shaft-like structure in a hair follicle germ in cell culture including: inoculating epithelial cells and mesenchymal cells; and co-culturing the epithelial cells and the mesenchymal cells to form the hair follicle germ, the method including promoting the formation of the hair shaft-like structure in the hair follicle germ by maintaining the epithelial cells and the mesenchymal cells in a culture solution in which (a) laminin and entactin, and/or (b) type IV collagen is dispersed. According to the one embodiment of the present invention, there is provided a method of promoting the formation of a hair shaft-like structure in a hair follicle germ in vitro simply and within a short period of time.

In order to solve the above-mentioned problem, according to one embodiment of the present invention, in still another aspect, there is provided a method of using (a) laminin and entactin, and/or (b) type IV collagen, for promoting formation of a hair shaft-like structure in a hair follicle germ in cell culture including: inoculating epithelial cells and mesenchymal cells; and co-culturing the epithelial cells and the mesenchymal cells to form the hair follicle germ. According to the one embodiment of the present invention, there is provided a method of using the (a) laminin and entactin, and/or the (b) type IV collagen, for promoting the formation of a hair shaft-like structure in a hair follicle germ in vitro simply and within a short period of time.

In order to solve the above-mentioned problem, according to one embodiment of the present invention, there is provided a hair follicle germ, including epithelial cells and mesenchymal cells, the hair follicle germ having a hair shaft-like structure, being free of an arrector pili muscle structure and/or a sebaceous gland structure, and not yet being transplanted to a living body. According to the one embodiment of the present invention, there is provided a hair follicle germ having a hair shaft-like structure formed in vitro simply and within a short period of time.

Advantageous Effects of Invention

According to the present invention, a hair follicle germ capable of forming a hair shaft-like structure in vitro simply and within a short period of time, and a method of producing the same are provided.

DESCRIPTION OF EMBODIMENTS

Figure 1A:
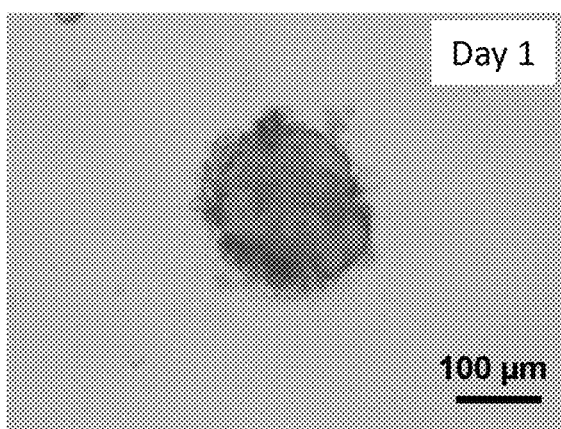
FIG. 1A is an explanatory diagram showing an example of a phase-contrast micrograph taken on day 1 of culture in example 1-1 according to one embodiment of the present invention.

Now, embodiments of the present invention will be described. The present invention is not limited to these embodiments.

In one aspect, a method according to one embodiment of the present invention (hereinafter referred to as "method of the present invention") encompasses a method of producing a hair follicle germ, including: inoculating epithelial cells and mesenchymal cells; maintaining the epithelial cells and the mesenchymal cells in a culture solution in which (a) laminin and entactin, and/or (b) type IV collagen is dispersed; and co-culturing the epithelial cells and the mesenchymal cells in a culture solution to form a hair follicle germ.

That is, the inventors of the present invention have made extensive investigations on technical means for producing a hair follicle germ in vitro, and as a result, have surprisingly found that, when in a culture solution, epithelial cells and mesenchymal cells are brought into contact with (a) laminin and entactin, and/or (b) type IV collagen dispersed in the culture solution, a hair follicle germ capable of forming a hair shaft-like structure in vitro can be produced simply and within a short period of time. Thus, the present invention has been completed.

Accordingly, in another aspect, the method of the present invention encompasses a method of promoting formation of a hair shaft-like structure in a hair follicle germ in cell culture including: inoculating epithelial cells and mesenchymal cells; and co-culturing the epithelial cells and the mesenchymal cells to form the hair follicle germ, the method including promoting the formation of the hair shaft-like structure in the hair follicle germ by maintaining the epithelial cells and the mesenchymal cells in a culture solution in which (a) laminin and entactin, and/or (b) type IV collagen is dispersed.

In addition, in still another aspect, the method of the present invention encompasses a method of using (a) laminin and entactin, and/or (b) type IV collagen, for promoting formation of a hair shaft-like structure in a hair follicle germ in cell culture including: inoculating epithelial cells and mesenchymal cells; and co-culturing the epithelial cells and the mesenchymal cells to form the hair follicle germ.

That is, the embodiments of the present invention encompass a use of (a) laminin and entactin, and/or (b) type IV collagen as an additive in a culture solution (more specifically a component dispersed in a culture solution) for promoting the formation of a hair shaft-like structure in a hair follicle germ.

The epithelial cells to be used in the method of the present invention are not particularly limited as long as the epithelial cells form a hair follicle germ through co-culture with the mesenchymal cells, but are preferably, for example, one or more kinds selected from the group consisting of: epithelial cells derived from a hair follicle tissue; epithelial cells derived from a skin tissue; and hair follicle epithelial cells induced from stem cells in a culture system.

The epithelial cells derived from a hair follicle tissue may be, for example, one or more kinds selected from the group consisting of: epithelial cells derived from the bulge region of a hair follicle tissue (e.g., cells of the outermost layer of an outer root sheath); and epithelial cells derived from the hair matrix portion of a hair follicle tissue. The epithelial cells derived from a skin tissue may be, for example, one or more kinds selected from the group consisting of: epidermal keratinocytes; and skin epithelial cells in a developmental period. The hair follicle epithelial cells induced from stem cells in a culture system may be, for example, hair follicle epithelial cells induced from induced Pluripotent Stem (iPS) cells, Embryonic Stem (ES) cells, or Embryonic Germ (EG) cells. The epithelial cells may be epithelial stem cells.

The epithelial cells express, for example, a hair growth-related gene. Specifically, the epithelial cells are identified as, for example, cells expressing a cytokeratin. When the epithelial cells are epithelial stem cells, the epithelial stem cells are identified as, for example, cells expressing one or more selected from the group consisting of: cytokeratin 15; and CD34. The epithelial cells may be primary cells collected from a living body, or may be cells cultured in advance (e.g., passaged cells and/or established cells).

The mesenchymal cells to be used in the method of the present invention are not particularly limited as long as the mesenchymal cells form a hair follicle germ through co-culture with the epithelial cells, but are preferably, for example, one or more kinds selected from the group consisting of: mesenchymal cells derived from a hair follicle tissue; mesenchymal cells derived from a skin tissue; and mesenchymal cells induced from stem cells in a culture system.

The mesenchymal cells derived from a hair follicle tissue may be, for example, one or more kinds selected from the group consisting of: dermal papilla cells; and dermal sheath cup cells. The mesenchymal cells derived from a skin tissue may be, for example, one or more kinds selected from the group consisting of: dermal sheath cells; and skin mesenchymal cells in a developmental period. The mesenchymal cells induced from stem cells in a culture system may be, for example, hair follicle mesenchymal cells induced from iPS cells, ES cells, or EG cells.

The mesenchymal cells express, for example, a hair growth-related gene. Specifically, the mesenchymal cells are identified as, for example, cells expressing one or more selected from the group consisting of: Versican; and alkaline phosphatase (ALP). The mesenchymal cells may be primary cells collected from a living body, or may be cells cultured in advance (e.g., passaged cells and/or established cells).

In the method of the present invention, co-culture of only the epithelial cells and the mesenchymal cells may be performed, but co-culture further including other cells may be performed. In this case, the other cells are not particularly limited as long as the effects of the present invention are obtained, but may be, for example, one or more selected from the group consisting of: pigment cells; pigment precursor cells; pigment stem cells; and pigment stem cells derived from pluripotent stem cells (e.g., iPS cells, ES cells, or Multilineage-differentiating stress-enduring (Muse) cells). In addition, a time at which the other cells are inoculated is not particularly limited as long as the time falls within a range in which a hair follicle germ containing the epithelial cells, the mesenchymal cells, and the other cells is formed.

In the method of the present invention, first, the epithelial cells and the mesenchymal cells are inoculated. In this regard, in the method described in Non-Patent Literature 1 above, induced pluripotent stem cells are inoculated. Accordingly, complicated operations for differentiating the induced pluripotent stem cells are essential in the method described in Non-Patent Literature 1. In contrast, in the method of the present invention, there is no need to use pluripotent stem cells. Accordingly, the method of the present invention need not include inoculating pluripotent stem cells. In addition, the method of the present invention need not include differentiating the pluripotent stem cells. In addition, the method of the present invention need not include culturing the pluripotent stem cells.

The inoculation of the epithelial cells and the mesenchymal cells is performed by placing the epithelial cells and the mesenchymal cells in a culture vessel. Specifically, a culture solution containing the epithelial cells and the mesenchymal cells (cell suspension) is placed in the culture vessel. In addition, the culture vessel includes a culture substrate on which the epithelial cells and the mesenchymal cells are sedimented (e.g., the bottom of the culture vessel, or a culture substrate arranged in the culture vessel and separate from the culture vessel), and hence it may be said that the epithelial cells and the mesenchymal cells are inoculated on the culture substrate.

In the inoculation of the epithelial cells and the mesenchymal cells, the epithelial cells and the mesenchymal cells may be simultaneously inoculated, or one type of the epithelial cells and the mesenchymal cells may be inoculated first, followed by inoculation of the other type of cells. That is, one type of the epithelial cells and the mesenchymal cells may be inoculated first without being brought into contact with the other type of cells, followed by inoculating the other type of cells to bring the other type of cells into contact with the one type of cells. In this case, it is preferred that the mesenchymal cells are inoculated first, and thereafter, the epithelial cells are inoculated.

Specifically, for example, first, a cell suspension containing the mesenchymal cells and free of the epithelial cells is placed in the culture vessel (e.g., a well of a 96-well plate) to inoculate the mesenchymal cells, and then a cell suspension containing the epithelial cells is placed in the culture vessel containing the mesenchymal cells to inoculate the epithelial cells. In this case, the cell suspension containing the epithelial cells may be free of the mesenchymal cells.

In addition, one type of the epithelial cells and the mesenchymal cells may be inoculated first, followed by culturing the one type of cells and thereafter followed by inoculating the other type of cells. That is, in this case, one type of the epithelial cells and the mesenchymal cells are inoculated and cultured first without being brought into contact with the other type of cells, followed by inoculating the other type of cells to start the co-culture of the one type and the other type.

When one type of the epithelial cells and the mesenchymal cells are inoculated first, followed by inoculating the other type of cells, a period of time from the inoculation of the one type of cells to the inoculation of the other type of cells (i.e., for example, a period of time from the inoculation of the one type of cells to the start of the co-culture of the one type of cells and the other type of cells) is not particularly limited as long as the period of time falls within a range in which the effects of the present invention are obtained, but may be, for example, 96 hours or less, and is preferably 72 hours or less, more preferably 48 hours or less, particularly preferably 24 hours or less.

The epithelial cells and the mesenchymal cells to be inoculated are preferably dispersed in a culture solution. In this case, the epithelial cells and the mesenchymal cells are mixed and dispersed in the culture solution. Individual cells dispersed in the culture solution are not bound to other cells, or are attached to other cells but are easily separated from the other cells by fluidizing the culture solution through an operation such as pipetting. The culture solution to be used in the method of the present invention is not particularly limited as long as the culture solution is a solution in which the epithelial cells and the mesenchymal cells are maintained alive and the effects of the present invention are obtained.

When one type of the epithelial cells and the mesenchymal cells are inoculated first, followed by inoculating the other type of cells, it is preferred that the one type of cells dispersed in a culture solution is inoculated first, followed by inoculating the other type of cells dispersed in a culture solution. Specifically, for example, a cell suspension in which the mesenchymal cells are dispersed and being free of the epithelial cells is placed in a culture vessel to inoculate the mesenchymal cells first, and then a cell suspension in which the epithelial cells are dispersed is placed in the culture vessel containing the mesenchymal cells to inoculate the epithelial cells.

The density of the epithelial cells and the mesenchymal cells to be inoculated is not particularly limited as long as the density falls within a range in which a hair follicle germ is formed in the subsequent co-culture, and is preferably, for example, such a density that the individual cells can be brought into contact with cells adjacent thereto in the culture vessel (in particular, in a state where the cells are sedimented on the culture substrate).

In the method of the present invention, the inoculated epithelial cells and mesenchymal cells are co-cultured in a culture solution to form a hair follicle germ containing the epithelial cells and the mesenchymal cells. That is, when the epithelial cells and the mesenchymal cells are co-cultured in the culture solution, the epithelial cells and the mesenchymal cells aggregate along with the lapse of culture time to form a hair follicle germ.

More specifically, the inoculated epithelial cells and mesenchymal cells are maintained in the culture solution in a state of being mixed and dispersed. After that, along with the lapse of culture time, the formation of binding of the epithelial cells to each other, the formation of binding of the mesenchymal cells to each other, and the formation of binding between the epithelial cells and the mesenchymal cells proceed. As a result, the epithelial cells aggregate to form an epithelial cell aggregate, and the mesenchymal cells aggregate to form a mesenchymal cell aggregate. In addition, binding between the epithelial cell aggregate and the mesenchymal cell aggregate is also formed in parallel with the formation of the epithelial cell aggregate and the mesenchymal cell aggregate. Thus, a hair follicle germ containing the epithelial cell aggregate and the mesenchymal cell aggregate is finally formed.

When one type (e.g., the mesenchymal cells) of the epithelial cells and the mesenchymal cells is inoculated first, followed by inoculating the other type (e.g., the epithelial cells) of cells, there may be efficiently formed a hair follicle germ containing a first cell aggregate formed through aggregation of the one type of cells, and a second cell aggregate formed through aggregation of the other type of cells and combined to the first cell aggregate.

In order to form a hair follicle germ in the method of the present invention, since the epithelial cells and the mesenchymal cells need to aggregate, the co-culture of the epithelial cells and the mesenchymal cells for forming the hair follicle germ is performed in a culture solution having fluidity.

The hair follicle germ is a cell aggregate that forms hair when transplanted to an animal. The hair follicle germ to be produced in the method of the present invention may be a hair follicle germ spheroid. The hair follicle germ spheroid is a cell mass having an approximately spherical shape.

The ratio of the number of the epithelial cells and the mesenchymal cells to the total number of the cells constituting the hair follicle germ is not particularly limited as long as the ratio falls within a range in which the effects of the present invention are obtained, but may be, for example, 50% or more, 70% or more, or 90% or more.

In this case, the ratio of the number of the epithelial cells and the mesenchymal cells to the total number of cells to be inoculated to produce the hair follicle germ may also be, for example, 50% or more, 70% or more, or 90% or more.

Similarly, the ratio of the number of the epithelial cells and the mesenchymal cells to the total number of cells to be co-cultured to form the hair follicle germ may also be, for example, 50% or more, 70% or more, or 90% or more.

In the method of the present invention, the epithelial cells and the mesenchymal cells may be co-cultured on a non-cell-adhesive culture substrate. In this case, during the co-culture, the epithelial cells and the mesenchymal cells float in the culture solution without adhering onto the culture substrate, or are attached to the culture substrate to such a degree as to be easily detached from the culture substrate by fluidizing the culture solution through an operation such as pipetting. The shape of each of the epithelial cells and the mesenchymal cells cultured on the non-cell-adhesive culture substrate is kept nearly spherical.

When the co-culture is performed on the non-cell-adhesive culture substrate, a hair follicle germ in a non-adherent state is formed. The hair follicle germ in a non-adherent state floats in the culture solution, or is attached to the culture substrate to such a degree as to be easily detached from the culture substrate by fluidizing the culture solution through an operation such as pipetting.

The culture vessel in which the epithelial cells and the mesenchymal cells are co-cultured is not particularly limited as long as the culture vessel allows the epithelial cells and the mesenchymal cells to form a hair follicle germ, but a relatively small well is preferably used, for example.

That is, the area of the bottom surface of one well to be used as the culture vessel may be, for example, 1,000 mm$^2$ or less, and is preferably 100 mm$^2$ or less, more preferably 50 mm$^2$ or less, particularly preferably 20 mm$^2$ or less.

The area of the bottom surface of the well may be, for example, 100 μm$^2$ or more, and is preferably 1,000 μm$^2$ or more, more preferably 10,000 μm$^2$ or more, particularly preferably 100,000 μm$^2$ or more.

The area of the bottom surface of the well may be specified by arbitrarily combining one of the above-mentioned lower limit values and one of the above-mentioned upper limit values.

Specifically, the area of the bottom surface of the well may be, for example, 100 μm$^2$ or more and 1,000 mm$^2$ or less, and is preferably 1,000 μm$^2$ or more and 100 mm$^2$ or less, more preferably 10,000 μm$^2$ or more and 50 mm$^2$ or less, particularly preferably 100,000 μm$^2$ or more and 20 mm$^2$ or less.

In the method of the present invention, one hair follicle germ may be formed in each culture vessel (e.g., each well) through the co-culture of the epithelial cells and the mesenchymal cells. That is, in this case, the epithelial cells and the mesenchymal cells inoculated in each culture vessel aggregate in the culture vessel to form one hair follicle germ.

In the method of the present invention, after the inoculation of the epithelial cells and the mesenchymal cells, the epithelial cells and the mesenchymal cells are maintained in a culture solution in which one or more selected from the group consisting of: (a) laminin and entactin; and (b) type IV collagen is dispersed.

That is, for example, the epithelial cells and the mesenchymal cells are maintained in a culture solution in which the (a) laminin and entactin is dispersed. In this case, the laminin and the entactin preferably include a complex of laminin and entactin.

In addition, for example, the epithelial cells and the mesenchymal cells are maintained in a culture solution in which the (b) type IV collagen is dispersed. In addition, for example, the epithelial cells and the mesenchymal cells are maintained in a culture solution in which the (a) laminin and entactin, and the (b) type IV collagen are dispersed.

The culture solution containing the dispersed (a) and/or (b) is prepared by adding, to a culture solution, a composition containing the (a) prepared in advance and/or a composition containing the (b) prepared in advance.

In the method of the present invention, the epithelial cells and the mesenchymal cells are maintained in the culture solution in which the (a) and/or the (b) is dispersed, and thus the epithelial cells and the mesenchymal cells are brought into contact with the (a) and/or the (b) in the culture solution.

That is, in a culture solution having fluidity, the epithelial cells and the mesenchymal cells are brought into contact with the (a) and/or the (b) dispersed in the culture solution. Specifically, the (a) and/or the (b) to be brought into contact with the epithelial cells and the mesenchymal cells in the method of the present invention is the (a) and/or the (b) dispersed in a culture solution having fluidity, and is not, for example, the (a) and/or the (b) forming a hydrogel in which the epithelial cells and the mesenchymal cells are embedded, the (a) and/or the (b) forming a hydrogel in the case where the epithelial cells and the mesenchymal cells are placed on the surface of the hydrogel, or the (a) and/or the (b) immobilized in advance on the culture substrate on which the epithelial cells and the mesenchymal cells are placed.

The method of the present invention may include bringing the epithelial cells and the mesenchymal cells placed on the surface of a hydrogel (e.g., a hydrogel formed of components including the (a) and/or the (b), or a hydrogel free of the (a) and/or the (b)) into contact with the (a) and/or the (b) dispersed in the culture solution. However, the method of the present invention need not include bringing the epithelial cells and the mesenchymal cells placed on the surface of a hydrogel formed of components including the (a) and/or the (b) into contact with the (a) and/or the (b) dispersed in the culture solution. In addition, the method of the present invention need not include bringing the epithelial cells and the mesenchymal cells placed on the surface of a hydrogel free of the (a) and/or the (b) into contact with the (a) and/or the (b) dispersed in the culture solution. In addition, the method of the present invention need not include bringing the epithelial cells and the mesenchymal cells placed on the surface of a hydrogel into contact with the (a) and/or the (b) dispersed in the culture solution.

The method of the present invention may include bringing the epithelial cells and the mesenchymal cells placed on the culture substrate on which the (a) and/or the (b) is immobilized into contact with the (a) and/or the (b) dispersed in the culture solution. However, the method of the present invention need not include bringing the epithelial cells and the mesenchymal cells placed on the culture substrate on which the (a) and/or the (b) is immobilized into contact with the (a) and/or the (b) dispersed in the culture solution.

In addition, the method of the present invention need not include embedding and culturing the epithelial cells and the mesenchymal cells in a hydrogel formed of components including the (a) and/or the (b) before the formation of the hair follicle germ. In addition, the method of the present invention need not include embedding and culturing the epithelial cells and the mesenchymal cells in a hydrogel free of the (a) and/or the (b) before the formation of the hair follicle germ. In addition, the method of the present invention need not include embedding and culturing the epithelial cells and the mesenchymal cells in a hydrogel before the formation of the hair follicle germ.

The cell suspension containing the epithelial cells and the mesenchymal cells to be used for the inoculation may contain the (a) and/or the (b), or may be free of the (a) and/or the (b). When the cell suspension at the time of the inoculation is free of the (a) and/or the (b), the epithelial cells and the mesenchymal cells are brought into contact with the (a) and/or the (b) dispersed in the culture solution by adding the (a) and/or the (b) to the culture solution after the inoculation.

That is, when the epithelial cells and the mesenchymal cells are simultaneously inoculated, the inoculation may be performed by placing a cell suspension containing the epithelial cells, the mesenchymal cells, and the (a) and/or the (b) in the culture vessel, or the inoculation may be performed first by placing a cell suspension containing the epithelial cells and the mesenchymal cells, and free of the (a) and/or the (b) in the culture vessel, followed by addition of the (a) and/or the (b) to the culture vessel.

In addition, when one type (e.g., the mesenchymal cells) of the epithelial cells and the mesenchymal cells are inoculated first, followed by inoculating the other type (e.g., the epithelial cells) of cells, each of the inoculation of the one type of cells and the inoculation of the other type of cells may be performed by placing a cell suspension containing the one type of cells or the other type of cells, and the (a) and/or the (b) in the culture vessel, or may be performed first by placing a cell suspension containing the one type of cells or the other type of cells, and free of the (a) and/or the (b) in the culture vessel, followed by addition of the (a) and/or the (b) to the culture vessel.

The concentration of the (a) laminin and entactin in the culture solution in which the epithelial cells and the mesenchymal cells are maintained is not particularly limited as long as the concentration falls within a range in which the effects of the present invention are obtained, but may be, for example, 1 µg/mL or more, and is preferably 3 µg/mL or more, particularly preferably 5 µg/mL or more.

In addition, the concentration of the (a) laminin and entactin in the above-mentioned culture solution may be, for example, 3,000 µg/mL or less, and is preferably 2,500 µg/mL or less, particularly preferably 2,000 µg/mL or less.

The concentration of the (a) laminin and entactin in the above-mentioned culture solution may be specified by arbitrarily combining any one of the above-mentioned lower limit values and any one of the above-mentioned upper limit values. That is, the concentration of the (a) laminin and entactin in the culture solution in which the epithelial cells and the mesenchymal cells are maintained may be, for example, 1 µg/mL or more and 3,000 µg/mL or less, and is preferably 3 µg/mL or more and 2,500 µg/mL or less, particularly preferably 5 µg/mL or more and 2,000 µg/mL or less.

The concentration of the (b) type IV collagen in the culture solution in which the epithelial cells and the mesenchymal cells are maintained is not particularly limited as long as the concentration falls within a range in which the effects of the present invention are obtained, but may be, for example, 1 µg/mL or more, and is preferably 3 µg/mL or more, particularly preferably 5 µg/mL or more.

In addition, the concentration of the (b) type IV collagen in the above-mentioned culture solution may be, for example, 1,000 µg/mL or less, and is preferably 700 µg/mL or less, particularly preferably 400 µg/mL or less.

The concentration of the (b) type IV collagen in the above-mentioned culture solution may be specified by arbitrarily combining any one of the above-mentioned lower limit values and any one of the above-mentioned upper limit values. That is, the concentration of the (b) type IV collagen in the culture solution in which the epithelial cells and the mesenchymal cells are maintained may be, for example, 1 μg/mL or more and 1,000 μg/mL or less, and is preferably 3 μg/mL or more and 700 μg/mL or less, particularly preferably 5 μg/mL or more and 400 μg/mL or less.

In the method of the present invention, the purpose of the dispersion of the (a) and/or the (b) in the culture solution is not to cause the culture solution to gelate, and hence the concentration of the (a) and/or the (b) in the culture solution may be lower than a concentration to be generally used for gelation. That is, the concentration of the (a) and/or the (b) in the culture solution in which the epithelial cells and the mesenchymal cells are maintained may be lower than a concentration for causing gelation of the entire culture solution.

A temperature at which the epithelial cells and the mesenchymal cells are maintained in the culture solution in which the (a) and/or the (b) is dispersed is not particularly limited as long as the temperature falls within a range in which the effects of the present invention are obtained, but is preferably, for example, a temperature suitable for the co-culture of the epithelial cells and the mesenchymal cells. Specifically, for example, the temperature is preferably a temperature of 30° C. or more and 45° C. or less, particularly preferably a temperature of 35° C. or more and 40° C. or less.

A period of time for which the epithelial cells and the mesenchymal cells are maintained in the culture solution in which the (a) and/or the (b) is dispersed (period of time for which the epithelial cells and the mesenchymal cells are maintained in the culture solution in which the (a) and/or the (b) is dispersed at the temperature suitable for the co-culture) is not particularly limited as long as the period of time falls within a range in which the effects of the present invention are obtained, but may be, for example, 30 minutes or more, and is preferably 40 minutes or more, more preferably 50 minutes or more, particularly preferably 60 minutes or more.

A time at which the epithelial cells and the mesenchymal cells are maintained in the culture solution in which the (a) and/or the (b) is dispersed is not particularly limited as long as the timing falls within a range in which the effects of the present invention are obtained, but it is preferable to start to maintain the epithelial cells and the mesenchymal cells in the culture solution in which the (a) and/or the (b) before the formation of a hair follicle germ.

Specifically, maintaining of the epithelial cells and the mesenchymal cells in the culture solution in which the (a) and/or the (b) is dispersed may be started, for example, before 28 hours have passed from a time point when the co-culture of the epithelial cells and the mesenchymal cells is started (i.e., a time point when the epithelial cells and the mesenchymal cells start to be maintained at the temperature suitable for the co-culture (e.g., preferably 35° C. or more and 39° C. or less, particularly preferably 36° C. or more and 38° C. or less)), and is preferably started before 24 hours have passed therefrom, more preferably started before 20 hours have passed therefrom, still more preferably started before 15 hours have passed therefrom, and particularly preferably started before 10 hours have passed therefrom.

That is, in each of the case of simultaneously inoculating the epithelial cells and the mesenchymal cells, and the case of first inoculating one type (e.g., the mesenchymal cells) of the epithelial cells and the mesenchymal cells, followed by inoculating the other type (e.g., the epithelial cells) of cells, the maintaining of the epithelial cells and the mesenchymal cells in the culture solution in which the (a) and/or the (b) is dispersed may be started before any one of the above-mentioned threshold times has passed from the time point when the co-culture of the epithelial cells and the mesenchymal cells is started (simultaneously with the start of the co-culture, or after the start of the co-culture and before any one of the above-mentioned threshold times has passed therefrom).

In addition, when one type (e.g., the mesenchymal cells) of the epithelial cells and the mesenchymal cells are inoculated first to start the culture of the one type of cells, followed by inoculating the other type (e.g., the epithelial cells) of cells to start the co-culture, the maintaining of the one type of cells in the culture solution in which the (a) and/or the (b) may be started before 28 hours have passed from a time point when the culture of the one type of cells is started (i.e., a time point when the one type of cells start to be maintained at a temperature suitable for the culture (e.g., preferably 35° C. or more and 39° C. or less, particularly preferably 36° C. or more and 38° C. or less)) (simultaneously with the start of the culture of the one type of cells, or after the start of the culture of the one type of cells and before the 28 hours have passed therefrom).

In this case, the maintaining of the one type of cells (cells inoculated first out of the epithelial cells and the mesenchymal cells) in the culture solution in which the (a) and/or the (b) is dispersed is, for example, preferably started before 24 hours have passed from the time point when the culture of the one type of cells is started, more preferably started before 18 hours have passed therefrom, still more preferably started before 12 hours have passed therefrom, and particularly preferably started simultaneously with the start of the culture of the one type of cells.

The method of the present invention may further include causing the inoculated epithelial cells and mesenchymal cells to be sedimented on a culture substrate in a culture solution, wherein the method includes maintaining the epithelial cells and the mesenchymal cells sedimented on the culture substrate in the culture solution in which the (a) and/or the (b) is dispersed.

That is, when the epithelial cells and the mesenchymal cells are inoculated on the culture substrate in a culture solution to which the (a) and/or the (b) is not added (in particular, in a culture solution to which the (a) is not added), for example, first, the inoculated epithelial cells and mesenchymal cells are sedimented on the culture substrate in the culture solution. After that, the (a) and/or the (b) is added to the culture solution, and the epithelial cells and the mesenchymal cells are maintained in the culture solution containing the dispersed (a) and/or (b).

In addition, when the epithelial cells and the mesenchymal cells are inoculated on the culture substrate in a culture solution to which the (a) and/or the (b) is added (in particular, in a culture solution to which the (a) is added), for example, first, the epithelial cells and the mesenchymal cells are sedimented on the culture substrate at a temperature (e.g., preferably 10° C. or less (specifically, for example, more than 0° C. and 10° C. or less), more preferably 7° C. or less, and particularly preferably 5° C. or less) lower than the temperature suitable for the co-culture, and then the epithelial cells and the mesenchymal cells are maintained in the culture solution containing the dispersed (a) and/or (b) at the temperature suitable for the co-culture.

A method for causing the epithelial cells and the mesenchymal cells to be sedimented on the culture substrate is not particularly limited, and for example, the epithelial cells and the mesenchymal cells may be sedimented on the culture substrate in the culture solution in the culture vessel by leaving the culture vessel including the culture substrate at rest, and/or subjecting the culture vessel including the culture substrate to centrifugal treatment.

In the method of the present invention, after the epithelial cells and the mesenchymal cells have been maintained in the culture solution in which the (a) and/or the (b) is dispersed as described above, the epithelial cells and the mesenchymal cells are co-cultured in a culture solution to form a hair follicle germ containing the epithelial cells and the mesenchymal cells.

In the co-culture, a culture solution to which the (a) and/or the (b) is added may be used, or a culture solution to which the (a) and/or the (b) is not added may be used. That is, the method of the present invention may include, after maintaining the epithelial cells and the mesenchymal cells in the culture solution in which the (a) and/or the (b) is dispersed, co-culturing the epithelial cells and the mesenchymal cells in a culture solution in which the concentration of the (a) and/or the (b) is lower than that of the culture solution in which the epithelial cells and the mesenchymal cells were maintained.

In this case, the epithelial cells and the mesenchymal cells are maintained in a culture solution containing the dispersed (a) and/or (b) at a first concentration, and then the epithelial cells and the mesenchymal cells are co-cultured in a culture solution in which the concentration of the (a) and/or the (b) is a second concentration lower than the first concentration.

The second concentration is not particularly limited as long as the second concentration is lower than the first concentration and falls within a range in which the effects of the present invention are obtained. The second concentration may be, for example, equal to or lower than one 5th of the first concentration, equal to or lower than one 10th thereof, equal to or lower than one 15th thereof, equal to or lower than one 20th thereof, equal to or lower than one 25th thereof, or equal to or lower than one 30th thereof.

The second concentration of the (a) may be, for example, less than 1 μg/mL, less than 0.2 μg/mL, or less than 0.1 μg/mL. The second concentration of the (b) may be, for example, less than 1 μg/mL, less than 0.2 μg/mL, or less than 0.1 μg/mL.

When the method of the present invention includes performing co-culture at the second concentration, the co-culture in the culture solution in which the concentration of the (a) and/or the (b) is the second concentration may be performed throughout a co-culture period until the formation of the hair follicle germ, or the co-culture in the culture solution in which the concentration of the (a) and/or the (b) is the second concentration may be performed only for part of the co-culture period.

When the concentration of the (a) and/or the (b) in the culture solution to be used for the co-culture is reduced, for example, the production cost of the hair follicle germ is effectively reduced, and further, complicated operations are reduced to improve operability.

In the method of the present invention, the (a) and/or the (b) dispersed in the culture solution are brought into contact with the epithelial cells and the mesenchymal cells, and then the epithelial cells and the mesenchymal cells are co-cultured, with the result that a hair follicle germ capable of forming a hair shaft-like structure in vitro is produced simply and within a short period of time. That is, when the hair follicle germ produced in the method of the present invention is further cultured, a hair shaft-like structure can be formed in the hair follicle germ.

In view of the foregoing, in the method of the present invention, after the epithelial cells and the mesenchymal cells have been maintained in the culture solution in which the (a) and/or the (b) is dispersed, a hair follicle germ having a hair shaft-like structure may be formed through the co-culture of the epithelial cells and the mesenchymal cells.

That is, in this case, even after the epithelial cells and the mesenchymal cells have aggregated to form a hair follicle germ, the co-culture of the epithelial cells and the mesenchymal cells (culture of the hair follicle germ) is continued until a hair shaft-like structure is formed in the hair follicle germ. As a result, a hair follicle germ having a hair shaft-like structure can be produced in vitro simply and within a short period of time.

Specifically, in the method of the present invention, for example, the hair follicle germ having a hair shaft-like structure may be formed before 480 hours have passed from the time point when the co-culture of the epithelial cells and the mesenchymal cells is started, preferably before 360 hours have passed therefrom, more preferably before 240 hours have passed therefrom, and particularly preferably before 170 hours have passed therefrom.

The hair shaft-like structure of the hair follicle germ is a string-like structural body formed in the hair follicle germ. The hair shaft-like structure may contain keratin. In addition, the hair shaft-like structure may contain melanin. In addition, the hair shaft-like structure may erupt from the hair follicle germ. In addition, the hair shaft-like structure may have a cuticle structure.

The length of the hair shaft-like structure of the hair follicle germ of the present invention is not particularly limited, but may be, for example, 30 μm or more, 50 μm or more, or 100 μm or more.

A hair follicle germ according to one embodiment of the present invention (hereinafter referred to as "hair follicle germ of the present invention") is a hair follicle germ including epithelial cells and mesenchymal cells, the hair follicle germ having a hair shaft-like structure, being free of an arrector pili muscle structure and/or a sebaceous gland structure, and not yet being transplanted to a living body. The hair follicle germ of the present invention is preferably produced by the method of the present invention described above.

The hair follicle germ of the present invention has a hair shaft-like structure despite not yet being transplanted to a living body. In this regard, hitherto, it has been possible to produce a hair follicle germ capable of forming a hair shaft-like structure in a living body after being transplanted to the living body. However, it has been difficult to form a hair shaft-like structure in a hair follicle germ outside a living body before its transplantation to the living body.

In the method described in Non-Patent Literature 1 above, skin organoids formed by culturing induced pluripotent stem cells have complex structures, such as an arrector pili muscle structure and a sebaceous gland structure. In contrast, the hair follicle germ of the present invention has a relatively simple structure.

That is, the hair follicle germ of the present invention is free of such arrector pili muscle structure and/or sebaceous gland structure as described in Non-Patent Literature 1 above. Specifically, the hair follicle germ of the present invention may be free of the arrector pili muscle structure, may be free of the sebaceous gland structure, or may be free of the arrector pili muscle structure and the sebaceous gland structure.

Applications of the hair follicle germ are not particularly limited, but for example, the hair follicle germ may be used for medical treatment, such as transplantation to a patient, or may be used for research relating to the formation of hair.

The living body to which the hair follicle germ is transplanted may be a human, or may be a non-human animal, but is preferably a human. The transplantation of the hair follicle germ to the living body is preferably transplantation to the skin of the living body.

The transplantation of the hair follicle germ to the living body may be applied to medical treatment, or may be applied to research. The transplantation of the hair follicle germ to the living body may be, for example, transplantation to a human patient suffering from or at a risk of suffering from a disease associated with hair loss, in order to treat or prevent the disease.

The disease associated with hair loss is not particularly limited, but may be, for example, one or more selected from the group consisting of: androgenetic alopecia (AGA); female androgenetic alopecia (FAGA); postpartum alopecia; diffuse alopecia; seborrheic alopecia; alopecia pityrodes; traction alopecia; metabolic alopecia; pressure alopecia; alopecia areata; alopecia neurotica; hair-pulling disorder; universalis alopecia; and symptomatic alopecia.

The hair follicle germ may be used for, for example, a search for a substance that may be used for the treatment or prevention of the disease associated with hair loss, a search for a substance involved in the disease, or research on the mechanism of the disease.

Next, specific Examples according to the embodiments of the present invention will be described.

Example 1

[Collection of Epithelial Cells and Mesenchymal Cells]

A dorsal skin tissue was collected from a C57BL/6 mouse embryo at embryonic day 18, and was subjected to dispase treatment by a partially modified version of a method reported by Nakao et al. (Koh-ei Toyoshima et al. Nature Communications, 3, 784, 2012) at 4° C. under the shaking condition of 30 rpm for 1 hour to separate the epithelial layer and mesenchymal layer of the skin tissue. After that, the epithelial layer was treated with 100 U/mL collagenase for 1 hour and 20 minutes and further treated with trypsin for 10 minutes to isolate epithelial cells. In addition, the mesenchymal layer was treated with 100 U/mL collagenase for 1 hour and 20 minutes to isolate mesenchymal cells.

[Culture]

In example 1-1, the epithelial cells and the mesenchymal cells were co-cultured using a culture solution containing laminin, entactin, and type IV collagen. First, DMEM/F12 medium (Advanced Dulbecco's Modified Eagle Medium/Ham's F-12, GIBCO® containing 1% GLUTAMAX® Supplement (L-glutamine supplement in powder form, GIBCO® and 0.2% NORMOCIN® (antimicrobial agent, INVIVOGEN®) was prepared as the culture solution.

Then, the epithelial cells and the mesenchymal cells in such amounts as to achieve a cell density of $5\times10^3$ cells/mL each (such amounts as to achieve a total cell density of $1\times10^4$ cells/mL) were suspended in the culture solution, and MATRIGEL® (MATRIGEL® Basement Membrane Matrix, CORNING®) in such an amount as to achieve a concentration of 1 v/v % was further added to prepare a cell suspension.

The Matrigel product used contained 10.6 mg/mL (protein amount measured by the Lowry method) of a soluble basement membrane matrix extracted from an Engelbreth-Holm-Swarm (EHS) mouse tumor, and a compositional ratio in the basement membrane matrix was as follows: 56% of laminin, 8% of entactin, and 31% of type IV collagen.

Accordingly, it is calculated that the cell suspension having added thereto 1 v/v % of the Matrigel product contained 59 μg/mL of laminin, 8 μg/mL of entactin, and 33 μg/mL of type IV collagen.

100 μL of the cell suspension was placed in each well of a 96-well plate (Prime surface (trademark), Sumitomo Bakelite Co., Ltd.) to inoculate the epithelial cells and the mesenchymal cells. Immediately after the inoculation, the 96-well plate was transferred into a refrigerator at 4° C. and left at rest for 20 minutes. As a result of being left at rest, the epithelial cells and the mesenchymal cells were sedimented on the bottom surface of each well in a state of being allowed to be brought into contact with each other in the cooled culture solution in the refrigerator. After that, the 96-well plate was transferred to an incubator at 37° C., and co-culture of the epithelial cells and the mesenchymal cells was started in the incubator. The co-culture was performed for 12 days.

In the co-culture, the culture solution was changed once every 2 days. The culture solution was changed by first removing almost all of the culture solution from each well, and then adding 100 μL of DMEM/F12 medium free of Matrigel and containing 1% GultaMax Supplement and 0.2% Normocin to each well as a fresh culture solution.

In addition, in example 1-2 for comparison, the epithelial cells and the mesenchymal cells were co-cultured in the same manner as in example 1-1 described above except that Matrigel was not added to the cell suspension at the time of the inoculation (i.e., only the culture solution free of Matrigel was used).

[Results]

Figure 1B:
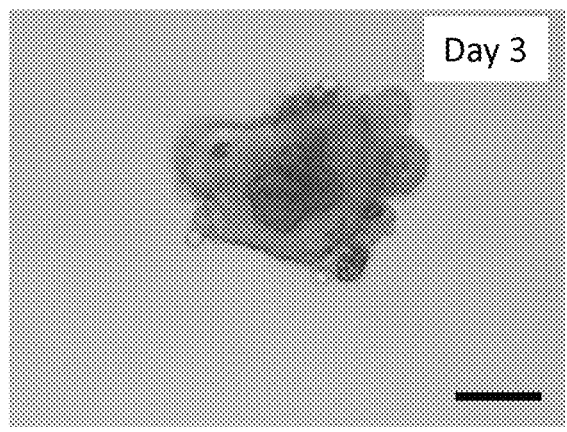
FIG. 1B is an explanatory diagram showing an example of a phase-contrast micrograph taken on day 3 of culture in example 1-1 according to one embodiment of the present invention.
Figure 1C:
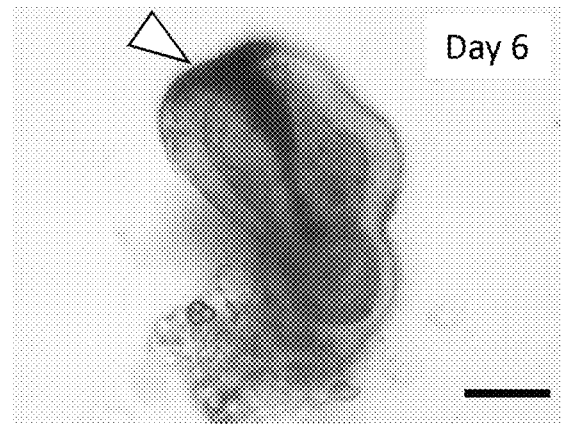
FIG. 1C is an explanatory diagram showing an example of a phase-contrast micrograph taken on day 6 of culture in example 1-1 according to one embodiment of the present invention.
Figure 1D:
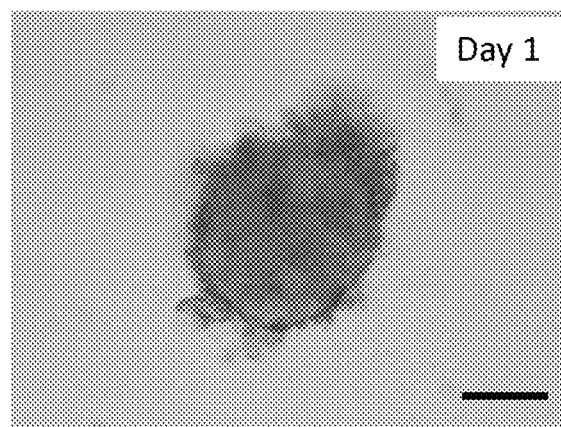
FIG. 1D is an explanatory diagram showing an example of a phase-contrast micrograph taken on day 1 of culture in example 1-2 according to one embodiment of the present invention.
Figure 1E:
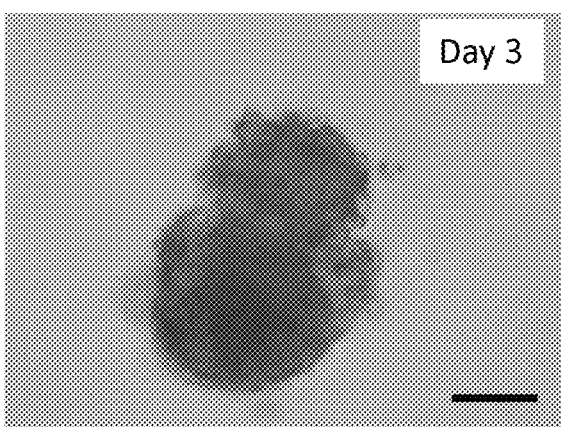
FIG. 1E is an explanatory diagram showing an example of a phase-contrast micrograph taken on day 3 of culture in example 1-2 according to one embodiment of the present invention.
Figure 1F:
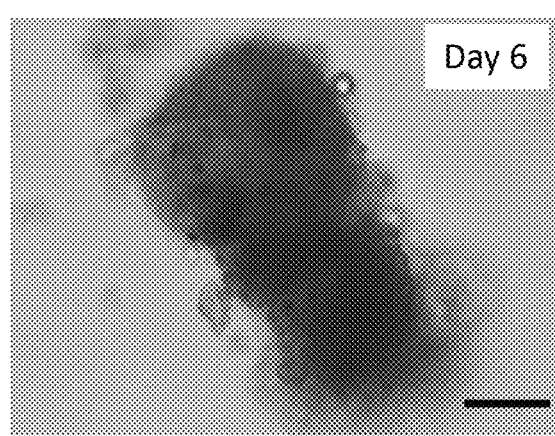
FIG. 1F is an explanatory diagram showing an example of a phase-contrast micrograph taken on day 6 of culture in example 1-2 according to one embodiment of the present invention.

FIG. 1A, FIG. 1B, and FIG. 1C show phase-contrast micrographs taken on day 1 of culture, day 3 of culture, and day 6 of culture, respectively, in the co-culture in one well of example 1-1. FIG. 1D, FIG. 1E, and FIG. 1F show phase-contrast micrographs taken on day 1 of culture, day 3 of culture, and day 6 of culture, respectively, in the co-culture in one well of example 1-2. In each of FIG. 1A to FIG. 1F, the scale bar represents 100 μm.

As shown in FIG. 1D to FIG. 1F, in example 1-2, a hair follicle germ having a hair shaft-like structure was not formed. In contrast, as shown in FIG. 1A to FIG. 1C, in example 1-1, a hair follicle germ having a hair shaft-like structure was formed. That is, as indicated by an arrowhead in FIG. 1C, the hair follicle germ on day 6 of culture had a hair shaft-like structure formed therein.

Figure 2A:
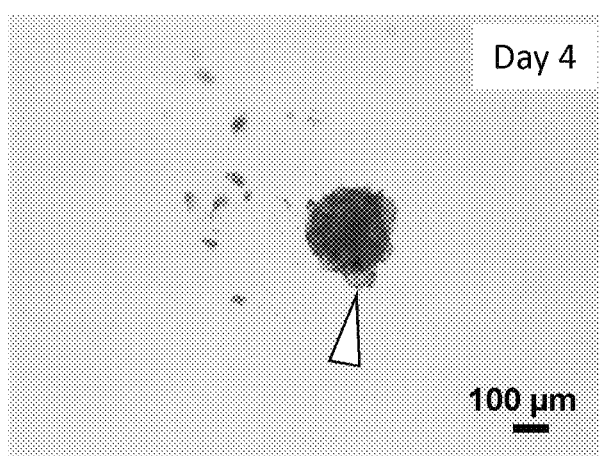
FIG. 2A is an explanatory diagram showing an example of a phase-contrast micrograph taken on day 4 of culture in example 1-1 according to one embodiment of the present invention.
Figure 2B:
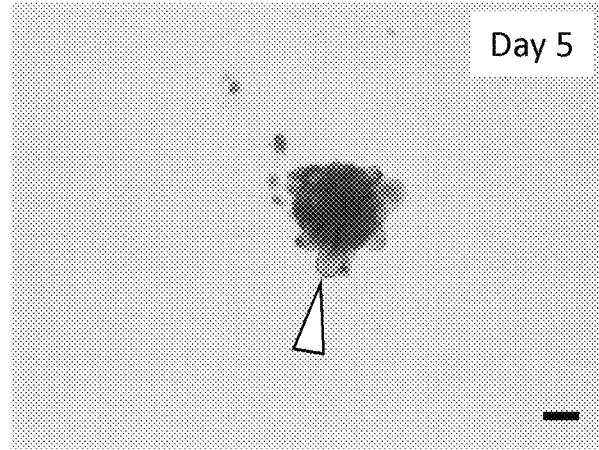
FIG. 2B is an explanatory diagram showing an example of a phase-contrast micrograph taken on day 5 of culture in example 1-1 according to one embodiment of the present invention.
Figure 2C:
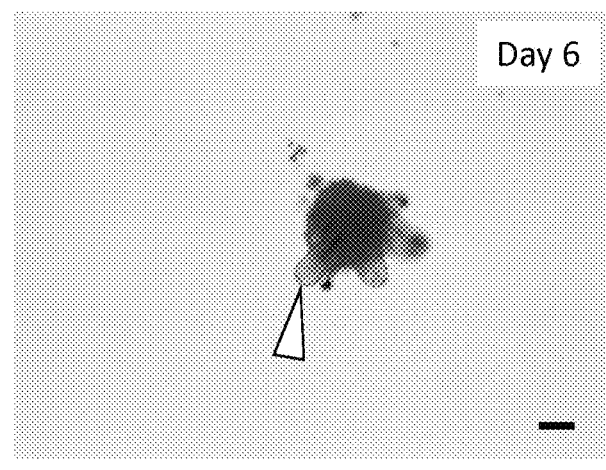
FIG. 2C is an explanatory diagram showing an example of a phase-contrast micrograph taken on day 6 of culture in example 1-1 according to one embodiment of the present invention.

In addition, FIG. 2A, FIG. 2B, and FIG. 2C show phase-contrast micrographs taken on day 4 of culture, day 5 of culture, and day 6 of culture, respectively, in the co-culture system in another well of example 1-1. In each of FIG. 2A to FIG. 2C, the scale bar represents 100 μm. As indicated by arrowheads in FIG. 2A to FIG. 2C, in example 1-1, the formation of a hair shaft-like structure was recognized on day 4 of culture, and then the hair shaft-like structure elongated along with the lapse of culture time.

In addition, the formation efficiency of hair shaft-like structures in hair follicle germs on day 10 of culture was evaluated. That is, the number of hair follicle germs each having a hair shaft-like structure formed therein on day 10 of culture was divided by the total number of hair follicle germs and multiplied by 100 to calculate a hair shaft-like structure formation ratio (%).

The results were as described below. In example 1-2, the formation of a hair shaft-like structure was not recognized in any of the 96 hair follicle germs, and hence the hair shaft-like structure formation ratio was 0 (zero) %. In contrast, in example 1-1, the formation of a hair shaft-like structure was recognized in 88 hair follicle germs out of the 96 hair follicle germs, and hence the hair shaft-like structure formation ratio was 92%.

Figure 3:
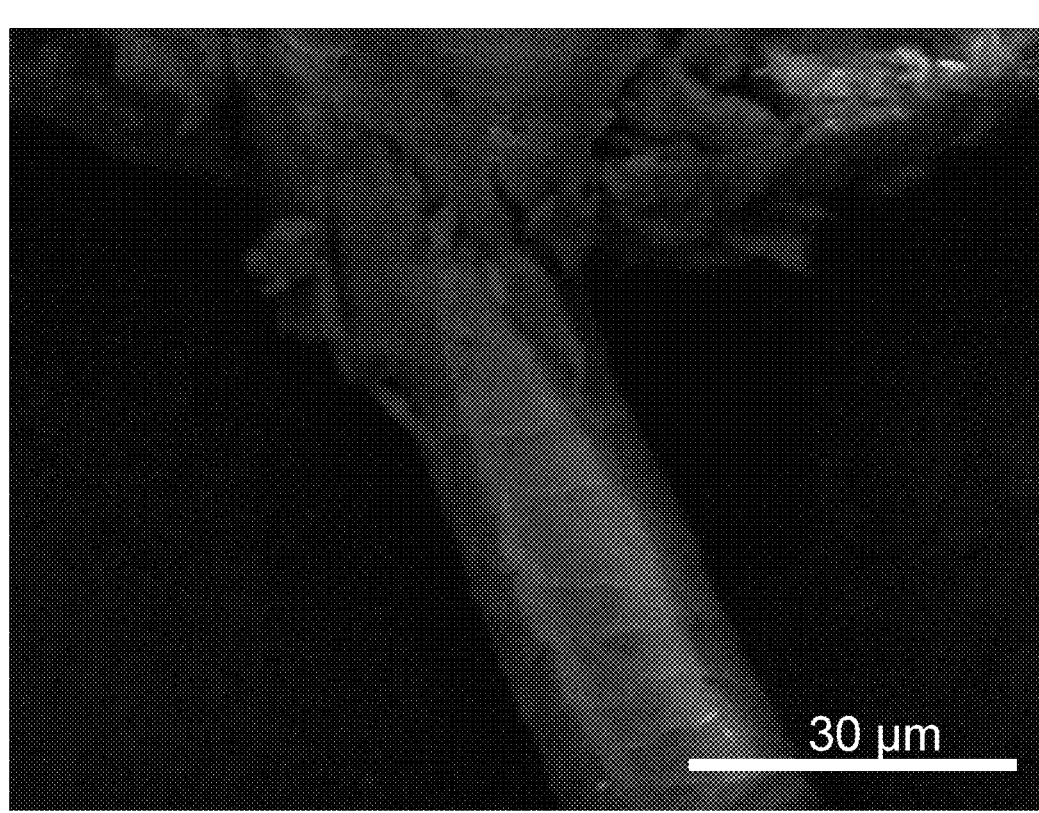
FIG. 3 is an explanatory diagram showing an example of a phase-contrast micrograph taken on day 12 of culture in example 1-1 according to one embodiment of the present invention.

FIG. 3 shows a scanning electron micrograph of a hair shaft-like structure formed in a hair follicle germ on day 12 of culture in example 1-1. In FIG. 3, the scale bar represents 30 μm. As shown in FIG. 3, the hair shaft-like structure formed in the hair follicle germ had a cuticle structure which is a characteristic structure of a hair shaft of a living body.

Example 2

[Collection of Epithelial Cells and Mesenchymal Cells]

Epithelial cells and mesenchymal cells were prepared in the same manner as in Example 1 described above.

[Culture]

In example 2-1, the epithelial cells and the mesenchymal cells were inoculated in a culture solution containing laminin, entactin, and type IV collagen in the same manner as in example 1-1 of Example 1 described above. That is, first, DMEM/F12 medium containing 1% GultaMax Supplement and 0.2% Normocin was prepared as the culture solution.

Then, the epithelial cells and the mesenchymal cells in such amounts as to achieve a cell density of $5 \times 10^3$ cells/mL each (such amounts as to achieve a total cell density of $1 \times 10^4$ cells/mL) were suspended in the culture solution, and Matrigel in such an amount as to achieve a concentration of 1 v/v % was further added to prepare a cell suspension.

100 μL of the cell suspension was placed in each well of a 96-well plate to inoculate the epithelial cells and the mesenchymal cells. Immediately after the inoculation, the 96-well plate was transferred into a refrigerator at 4° C. and left at rest for 20 minutes to cause the epithelial cells and the mesenchymal cells to be sedimented in each well. After that, the 96-well plate was transferred to an incubator at 37° C., and co-culture of the epithelial cells and the mesenchymal cells was started in the incubator.

After 1 day of culture, 100 μL of DMEM/F12 medium containing 1% GultaMax Supplement and 0.2% Normocin, and free of Matrigel, was added to each well. As a result, the amount of the culture solution in each well became about 200 μL.

After that, the culture solution was changed once every 2 days. The culture solution was changed by first removing 100 μL of the culture solution from each well, and then adding 100 μL of DMEM/F12 medium free of Matrigel and containing 1% GultaMax Supplement and 0.2% Normocin to each well as a fresh culture solution.

In example 2-2, the epithelial cells and the mesenchymal cells were inoculated in a culture solution free of laminin, entactin, and type IV collagen, and then laminin, entactin, and type IV collagen were added to the culture solution on day 1 of culture.

That is, first, epithelial cells and mesenchymal cells in such amounts as to achieve a cell density of $5 \times 10^3$ cells/mL each (such amounts as to achieve a total cell density of $1 \times 10^4$ cells/mL) were suspended in DMEM/F12 medium containing 1% GultaMax Supplement and 0.2% Normocin to prepare a cell suspension.

Then, 100 μL of the cell suspension was placed in each well of a 96-well plate to inoculate the epithelial cells and the mesenchymal cells. Immediately after the inoculation, the 96-well plate was transferred to an incubator at 37° C., and co-culture of the epithelial cells and the mesenchymal cells was started.

After 1 day of culture (specifically, at the time point when about 22 hours had passed from the start of the co-culture (time point when the 96-well plate was transferred to the incubator at 37° C.)), 100 μL of DMEM/F12 medium containing 1% GultaMax Supplement, 0.2% Normocin, and 2 v/v % Matrigel was added to each well. As a result, the amount of the culture solution in each well became about 200 μL, and the Matrigel concentration in the culture solution became about 1 v/v %.

Further, immediately after the addition of Matrigel, the 96-well plate was transferred into a refrigerator at 4° C. and left at rest for 20 minutes. After that, the 96-well plate was transferred to an incubator at 37° C., and the co-culture of the epithelial cells and the mesenchymal cells was continued in the incubator. The culture solution was changed in the same manner as in example 2-1 described above.

In example 2-3, the epithelial cells and the mesenchymal cells were inoculated in a culture solution free of laminin, entactin, and type IV collagen, and then laminin, entactin, and type IV collagen were added to the culture solution on day 3 of culture.

That is, in the same manner as in example 2-2 described above, 100 μL of a cell suspension containing the epithelial cells and the mesenchymal cells was placed in each well of a 96-well plate to inoculate the epithelial cells and the mesenchymal cells, and co-culture was started in an incubator at 37° C.

After 1 day of culture, 100 μL of DMEM/F12 medium containing 1% GultaMax Supplement and 0.2% Normocin was added to each well. As a result, the amount of the culture solution in each well became about 200 μL.

After 3 days of culture (specifically, at the time point when about 69 hours had passed from the start of the co-culture), first, 100 μL of the culture solution was removed from each well, and then 100 μL of DMEM/F12 medium containing 1% GultaMax Supplement, 0.2% Normocin, and 2 v/v % Matrigel was added. As a result, the Matrigel concentration in the culture solution in each well became about 1 v/v %.

Further, immediately after the addition of Matrigel, the 96-well plate was transferred into a refrigerator at 4° C. and left at rest for 20 minutes. After that, the 96-well plate was transferred to an incubator at 37° C., and the co-culture of the epithelial cells and the mesenchymal cells was continued in the incubator. The culture solution was changed in the same manner as in example 2-1 described above.

[Results]

Figure 4A:
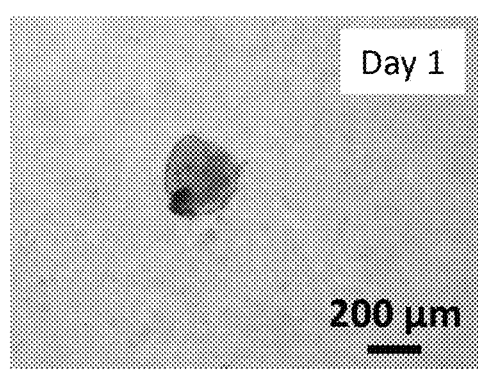
FIG. 4A is an explanatory diagram showing an example of a phase-contrast micrograph taken on day 1 of culture in example 2-1 according to one embodiment of the present invention.
Figure 4B:
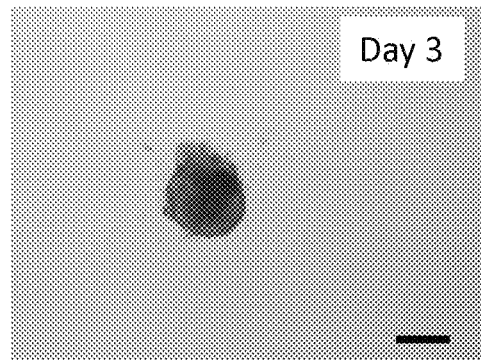
FIG. 4B is an explanatory diagram showing an example of a phase-contrast micrograph taken on day 3 of culture in example 2-1 according to one embodiment of the present invention.
Figure 4C:
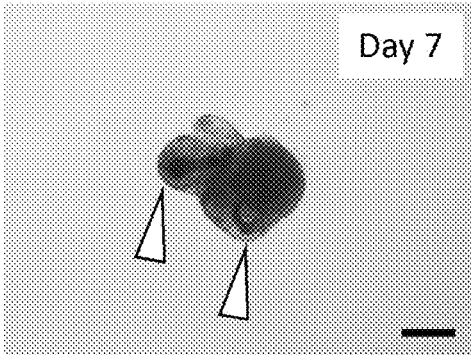
FIG. 4C is an explanatory diagram showing an example of a phase-contrast micrograph taken on day 7 of culture in example 2-1 according to one embodiment of the present invention.
Figure 4D:
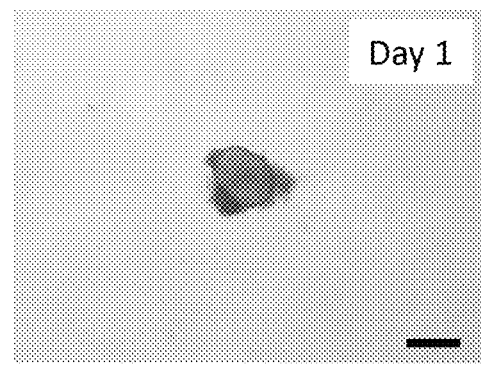
FIG. 4D is an explanatory diagram showing an example of a phase-contrast micrograph taken on day 1 of culture in example 2-2 according to one embodiment of the present invention.
Figure 4E:
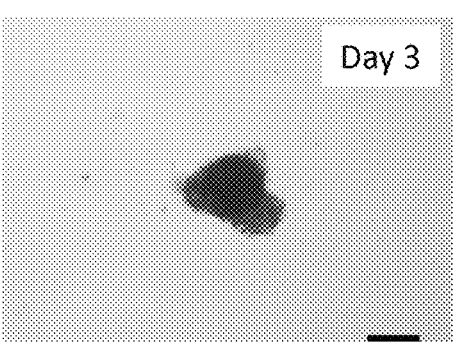
FIG. 4E is an explanatory diagram showing an example of a phase-contrast micrograph taken on day 3 of culture in example 2-2 according to one embodiment of the present invention.
Figure 4F:
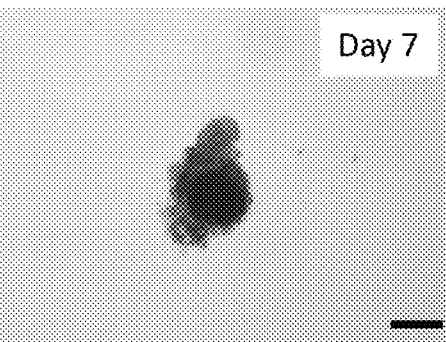
FIG. 4F is an explanatory diagram showing an example of a phase-contrast micrograph taken on day 7 of culture in example 2-2 according to one embodiment of the present invention.
Figure 4G:
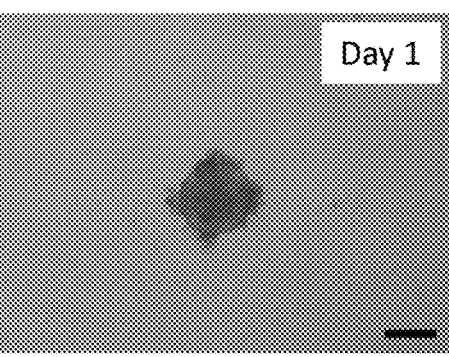
FIG. 4G is an explanatory diagram showing an example of a phase-contrast micrograph taken on day 1 of culture in example 2-3 according to one embodiment of the present invention.
Figure 4H:
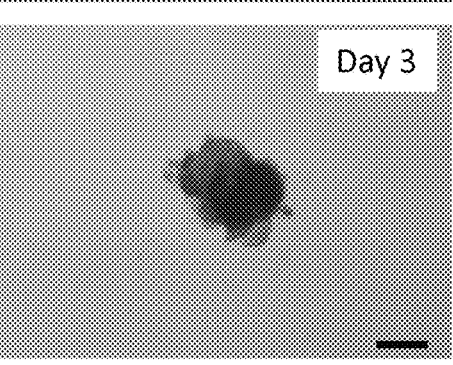
FIG. 4H is an explanatory diagram showing an example of a phase-contrast micrograph taken on day 3 of culture in example 2-3 according to one embodiment of the present invention.
Figure 4I:
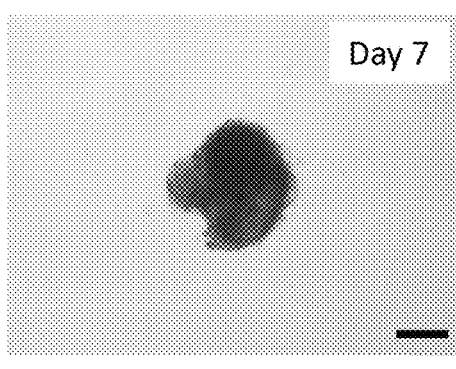
FIG. 4I is an explanatory diagram showing an example of a phase-contrast micrograph taken on day 7 of culture in example 2-3 according to one embodiment of the present invention.
Figure 5A:
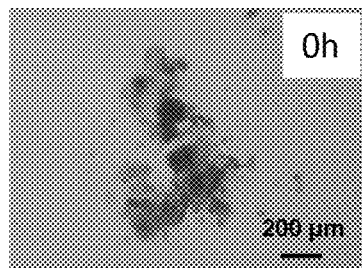
FIG. 5A is an explanatory diagram showing an example of a phase-contrast micrograph taken on day 3 of culture in example 3-1 according to one embodiment of the present invention.
Figure 5B:
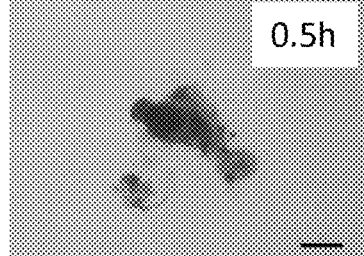
FIG. 5B is an explanatory diagram showing an example of a phase-contrast micrograph taken on day 3 of culture in example 3-2 according to one embodiment of the present invention.
Figure 5C:
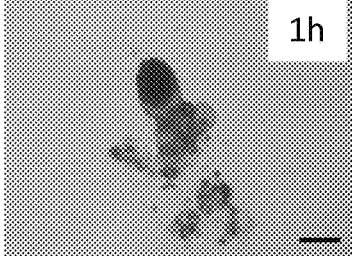
FIG. 5C is an explanatory diagram showing an example of a phase-contrast micrograph taken on day 3 of culture in example 3-3 according to one embodiment of the present invention.
Figure 5D:
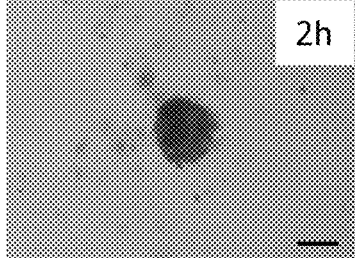
FIG. 5D is an explanatory diagram showing an example of a phase-contrast micrograph taken on day 3 of culture in example 3-4 according to one embodiment of the present invention.
Figure 5E:
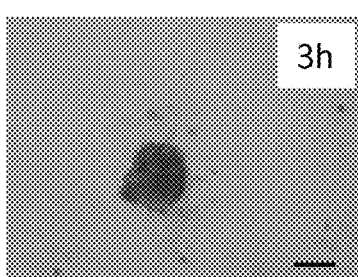
FIG. 5E is an explanatory diagram showing an example of a phase-contrast micrograph taken on day 3 of culture in example 3-5 according to one embodiment of the present invention.
Figure 5F:
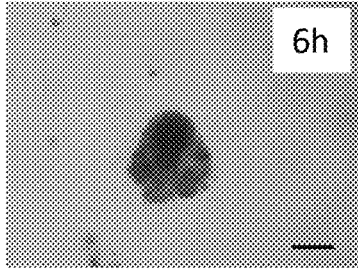
FIG. 5F is an explanatory diagram showing an example of a phase-contrast micrograph taken on day 3 of culture in example 3-6 according to one embodiment of the present invention.
Figure 5G:
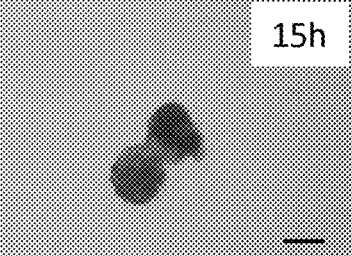
FIG. 5G is an explanatory diagram showing an example of a phase-contrast micrograph taken on day 3 of culture in example 3-7 according to one embodiment of the present invention.
Figure 5H:
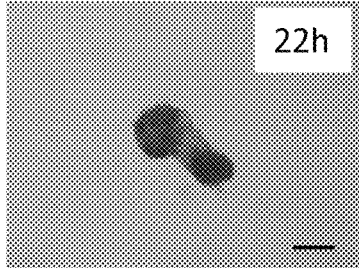
FIG. 5H is an explanatory diagram showing an example of a phase-contrast micrograph taken on day 3 of culture in example 3-8 according to one embodiment of the present invention.
Figure 6A:
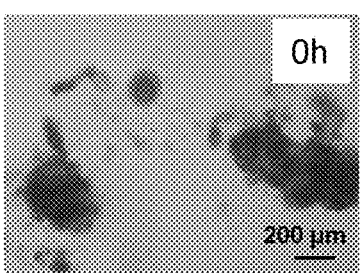
FIG. 6A is an explanatory diagram showing an example of a phase-contrast micrograph taken on day 8 of culture in example 3-1 according to one embodiment of the present invention.
Figure 6B:
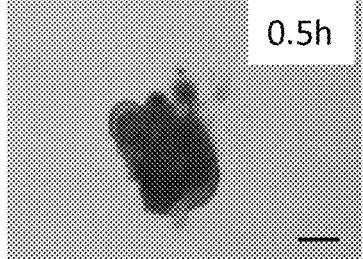
FIG. 6B is an explanatory diagram showing an example of a phase-contrast micrograph taken on day 8 of culture in example 3-2 according to one embodiment of the present invention.
Figure 6C:
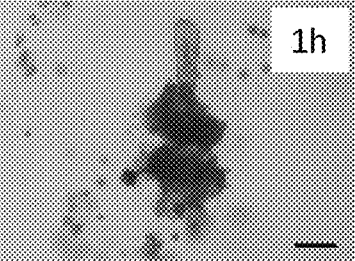
FIG. 6C is an explanatory diagram showing an example of a phase-contrast micrograph taken on day 8 of culture in example 3-3 according to one embodiment of the present invention.
Figure 6D:
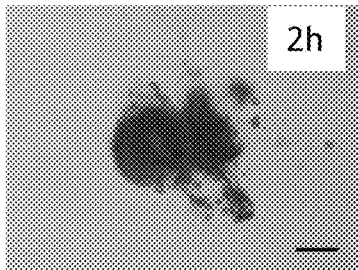
FIG. 6D is an explanatory diagram showing an example of a phase-contrast micrograph taken on day 8 of culture in example 3-4 according to one embodiment of the present invention.
Figure 6E:
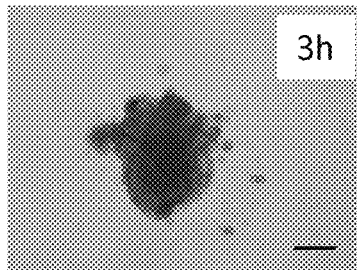
FIG. 6E is an explanatory diagram showing an example of a phase-contrast micrograph taken on day 8 of culture in example 3-5 according to one embodiment of the present invention.
Figure 6F:
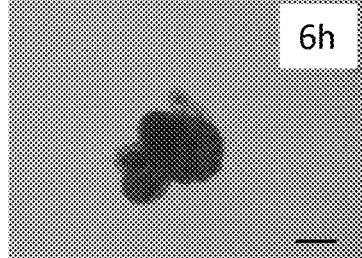
FIG. 6F is an explanatory diagram showing an example of a phase-contrast micrograph taken on day 8 of culture in example 3-6 according to one embodiment of the present invention.
Figure 6G:
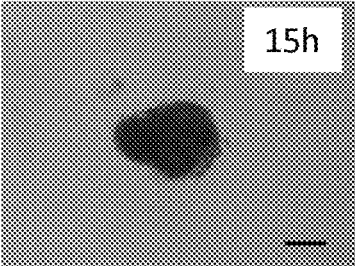
FIG. 6G is an explanatory diagram showing an example of a phase-contrast micrograph taken on day 8 of culture in example 3-7 according to one embodiment of the present invention.
Figure 6H:
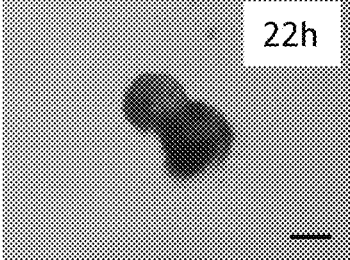
FIG. 6H is an explanatory diagram showing an example of a phase-contrast micrograph taken on day 8 of culture in example 3-8 according to one embodiment of the present invention.

FIG. 4A, FIG. 4B, and FIG. 4C show phase-contrast micrographs taken on day 1 of culture, day 3 of culture, and day 7 of culture, respectively, in the co-culture of example 2-1. FIG. 4D, FIG. 4E, and FIG. 4F show phase-contrast micrographs taken on day 1 of culture, day 3 of culture, and day 7 of culture, respectively, in the co-culture of example 2-2. FIG. 4G, FIG. 4H, and FIG. 4I show phase-contrast micrographs taken on day 1 of culture, day 3 of culture, and day 7 of culture, respectively, in the co-culture of example 2-3. In each of FIG. 4A to FIG. 4I, the scale bar represents 200 μm.

As shown in FIG. 4A to FIG. 4C, in example 2-1, a hair follicle germ having hair shaft-like structures was formed. That is, as indicated by arrowheads in FIG. 4C, the hair follicle germ on day 7 of culture had hair shaft-like structures formed therein. In contrast, as shown in FIG. 4D to FIG. 4I, in each of example 2-2 and example 2-3, the hair follicle germ on day 7 of culture had no hair shaft-like structure formed therein.

Example 3

[Collection of Epithelial Cells and Mesenchymal Cells]

Epithelial cells and mesenchymal cells were prepared in the same manner as in Example 1 described above.

[Culture]

In example 3-1, first, the epithelial cells and the mesenchymal cells were inoculated in a culture solution free of laminin, entactin, and type IV collagen, and then laminin, entactin, and type IV collagen were added to the culture solution immediately after the inoculation (after 0 hours from the inoculation).

That is, first, epithelial cells and mesenchymal cells in such amounts as to achieve a cell density of $5 \times 10^3$ cells/mL each (such amounts as to achieve a total cell density of $1 \times 10^4$ cells/mL) were suspended in DMEM/F12 medium containing 1% GultaMax Supplement and 0.2% Normocin to prepare a cell suspension.

Then, 100 µL of the cell suspension was placed in each well of a 96-well plate to inoculate the epithelial cells and the mesenchymal cells. Then, 100 µL of DMEM/F12 medium containing 1% GultaMax Supplement, 0.2% Normocin, and 2 v/v % Matrigel was added to each well immediately after the inoculation. As a result, the amount of the culture solution in each well became 200 µL, and the Matrigel concentration in the culture solution became 1 v/v %.

Immediately before the addition of the culture solution containing Matrigel, and immediately after the inoculation, some of the epithelial cells and the mesenchymal cells in each well had not yet been sedimented on the bottom surface of the well, and were floating in the culture solution.

After that, the 96-well plate was transferred to an incubator at 37° C., and co-culture of the epithelial cells and the mesenchymal cells was started in the incubator. The culture solution was changed in the same manner as in example 2-1 of Example 2 described above.

In example 3-2, first, co-culture was started by inoculating the epithelial cells and the mesenchymal cells in a culture solution free of laminin, entactin, and type IV collagen, and then laminin, entactin, and type IV collagen were added to the culture solution at the time point when 0.5 hour had passed from the start of the co-culture.

That is, first, epithelial cells and mesenchymal cells in such amounts as to achieve a cell density of $5 \times 10^3$ cells/mL each (such amounts as to achieve a total cell density of $1 \times 10^4$ cells/mL) were suspended in DMEM/F12 medium containing 1% GultaMax Supplement and 0.2% Normocin to prepare a cell suspension.

100 µL of the cell suspension was placed in each well of a 96-well plate to inoculate the epithelial cells and the mesenchymal cells. Immediately after the inoculation, the 96-well plate was transferred to an incubator at 37° C., and co-culture of the epithelial cells and the mesenchymal cells was started in the incubator.

At the time point when 0.5 hour had passed from the start of the co-culture, 100 µL of DMEM/F12 medium containing 1% GultaMax Supplement, 0.2% Normocin, and 2 v/v % Matrigel was added to each well. As a result, the amount of the culture solution in each well became about 200 µL, and the Matrigel concentration in the culture solution became 1 v/v %.

At the time point when 0.5 hour had passed from the start of the co-culture, immediately before the addition of the culture solution containing Matrigel, the epithelial cells and the mesenchymal cells in each well had already been sedimented on the bottom surface of the well.

After that, the co-culture of the epithelial cells and the mesenchymal cells was continued. The culture solution was changed in the same manner as in example 2-1 of Example 2 described above.

In example 3-3, the epithelial cells and the mesenchymal cells were co-cultured in the same manner as in example 3-2 described above except that laminin, entactin, and type IV collagen were added to the culture solution at the time point when 1 hour had passed from the start of the co-culture.

In example 3-4, the epithelial cells and the mesenchymal cells were co-cultured in the same manner as in example 3-2 described above except that laminin, entactin, and type IV collagen were added to the culture solution at the time point when 2 hours had passed from the start of the co-culture.

In example 3-5, the epithelial cells and the mesenchymal cells were co-cultured in the same manner as in example 3-2 described above except that laminin, entactin, and type IV collagen were added to the culture solution at the time point when 3 hours had passed from the start of the co-culture.

In example 3-6, the epithelial cells and the mesenchymal cells were co-cultured in the same manner as in example 3-2 described above except that laminin, entactin, and type IV collagen were added to the culture solution at the time point when 6 hours had passed from the start of the co-culture.

In example 3-7, the epithelial cells and the mesenchymal cells were co-cultured in the same manner as in example 3-2 described above except that laminin, entactin, and type IV collagen were added to the culture solution at the time point when 15 hours had passed from the start of the co-culture.

In example 3-8, the epithelial cells and the mesenchymal cells were co-cultured in the same manner as in example 3-2 described above except that laminin, entactin, and type IV collagen were added to the culture solution at the time point when 22 hours had passed from the start of the co-culture.

[Results]

FIG. 5A, FIG. 5B, FIG. 5C, FIG. 5D, FIG. 5E, FIG. 5F, FIG. 5G, and FIG. 5H show phase-contrast micrographs taken on day 3 of culture in the co-culture of example 3-1, example 3-2, example 3-3, example 3-4, example 3-5, example 3-6, example 3-7, and example 3-8, respectively. FIG. 6A, FIG. 6B, FIG. 6C, FIG. 6D, FIG. 6E, FIG. 6F, FIG. 6G, and FIG. 6H show phase-contrast micrographs taken on day 8 of culture in the co-culture of example 3-1, example 3-2, example 3-3, example 3-4, example 3-5, example 3-6, example 3-7, and example 3-8, respectively. In each of FIG. 5A to FIG. 5H, and FIG. 6A to FIG. 6H, the scale bar represents 200 µm.

As shown in FIG. 5A to FIG. 5H, and FIG. 6A to FIG. 6H, in all of the examples in which laminin, entactin, and type IV collagen were added to the culture solution at the time point when 0 hours to 22 hours had passed from the start of the co-culture (example 3-1 to example 3-8), a hair follicle germ having a hair shaft-like structure was formed. That is, as shown in FIG. 6A to FIG. 6H, in all the examples, the hair follicle germ on day 8 of culture had a hair shaft-like structure formed therein.

In addition, the hair shaft-like structure formation ratios were: 22% (2 out of 9 hair follicle germs) in example 3-1; 89% (8 out of 9 hair follicle germs) in example 3-2; 78% (7 out of 9 hair follicle germs) in example 3-3; 100% (9 out of 9 hair follicle germs) in example 3-4; 89% (8 out of 9 hair follicle germs) in example 3-5; 78% (7 out of 9 hair follicle germs) in example 3-6; 44% (4 out of 9 hair follicle germs) in example 3-7; and 22% (2 out of 9 hair follicle germs) in example 3-8.

A reason why the hair shaft-like structure formation efficiencies of example 3-7 and example 3-8, in which Matrigel was added at the time point when 15 hours or 22 hours had passed from the start of the co-culture, are lower than those of example 3-2 to example 3-6, in which Matrigel was added at the time point when 0.5 hour to 6 hours had passed, may be, for example, that the aggregation of the epithelial cells and the mesenchymal cells had already advanced at the time point when the Matrigel was added.

In addition, a reason why the hair shaft-like structure formation efficiency of example 3-1, in which Matrigel was added immediately after the start of the co-culture, is low may be, for example, that some of the epithelial cells and the mesenchymal cells had not been sedimented on the bottom surfaces of the wells, and were still in a floating state at the time point when the Matrigel was added.

In example 2-2 of Example 2 described above, although laminin, entactin, and type IV collagen were added to the culture solution at the time point when about 22 hours had passed from the start of the co-culture as in example 3-6, the formation of a hair shaft-like structure was not recognized in the hair follicle germ on day 6 of culture. A cause thereof may be, for example, an influence resulting from a difference between mouse individuals from which cells were collected.

Example 4

[Collection of Epithelial Cells and Mesenchymal Cells]

Epithelial cells and mesenchymal cells were prepared in the same manner as in Example 1 described above.

[Culture]

In example 4, the epithelial cells and the mesenchymal cells were co-cultured using a culture solution containing laminin and entactin. First, DMEM/F12 medium containing 1% GultaMax Supplement and 0.2% Normocin was prepared as the culture solution.

Then, the epithelial cells and the mesenchymal cells in such amounts as to achieve a cell density of $5 \times 10^3$ cells/mL each (such amounts as to achieve a total cell density of $1 \times 10^4$ cells/mL) were suspended in the culture solution, and a high concentration laminin/entactin complex (HIGH CONCENTRATION LAMININ/ENTACTIN COMPLEX, CORNING (trademark)) in such an amount as to achieve a concentration of 1 v/v % was further added to prepare a cell suspension.

The high concentration laminin/entactin complex product used contained 15.2 mg/mL of a soluble basement membrane matrix extracted from an EHS mouse tumor, contained a laminin/entactin complex at a purity of 90% or more according to SDS-PAGE, and contained laminin and entactin at equal molar ratios.

Accordingly, it is calculated that the cell suspension having added thereto 1 v/v % of the high concentration laminin/entactin complex product contained 137 µg/mL to 152 µg/mL of the laminin/entactin complex (i.e., 68 µg/mL to 76 µg/mL each of laminin and entactin).

That is, it is calculated that in the cell suspension of example 4, the content of laminin was from 115% to 129% of that in the cell suspension of example 1-1 of Example 1 described above, and the total content of laminin and entactin was from 204% to 227% of that in the cell suspension of example 1-1 of Example 1 described above.

100 µL of the cell suspension was placed in each well of a 96-well plate to inoculate the epithelial cells and the mesenchymal cells. Immediately after the inoculation, the 96-well plate was transferred into a refrigerator at 4° C. and left at rest for 20 minutes. As a result, the epithelial cells and the mesenchymal cells were sedimented on the bottom surface of each well in the cooled culture solution in the refrigerator. After that, the 96-well plate was transferred to an incubator at 37° C., and co-culture of the epithelial cells and the mesenchymal cells was started in the incubator. The culture solution was changed in the same manner as in example 1-1 of Example 1 described above.

[Results]

Figure 7A:
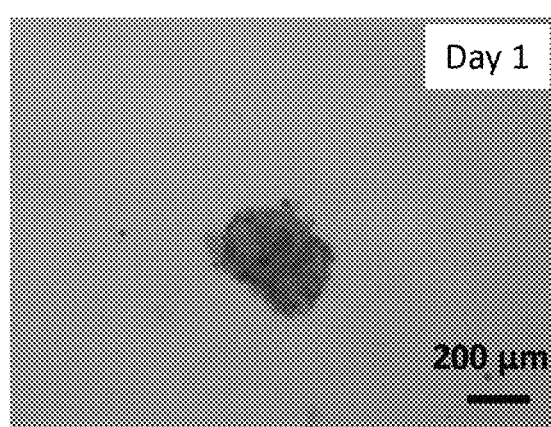
FIG. 7A is an explanatory diagram showing an example of a phase-contrast micrograph taken on day 1 of culture in example 4 according to one embodiment of the present invention.
Figure 7B:
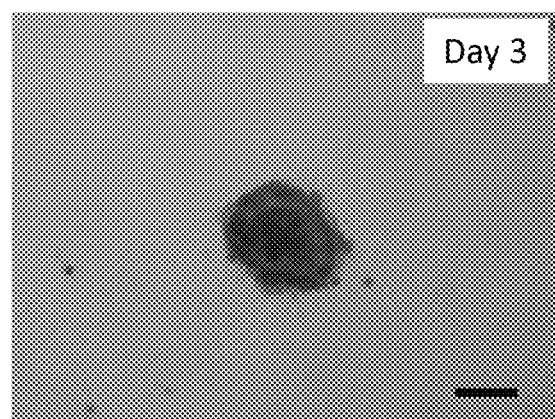
FIG. 7B is an explanatory diagram showing an example of a phase-contrast micrograph taken on day 3 of culture in example 4 according to one embodiment of the present invention.
Figure 7C:
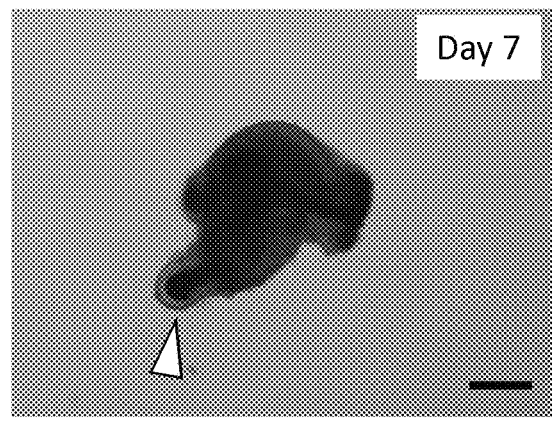
FIG. 7C is an explanatory diagram showing an example of a phase-contrast micrograph taken on day 7 of culture in example 4 according to one embodiment of the present invention.

FIG. 7A, FIG. 7B, and FIG. 7C show phase-contrast micrographs taken on day 1 of culture, day 3 of culture, and day 7 of culture, respectively, in the co-culture of example 4. In each of FIG. 1A to FIG. 7C, the scale bar represents 200 µm.

As shown in FIG. 7A to FIG. 7C, a hair follicle germ having a hair shaft-like structure was formed through use of the culture solution containing laminin and entactin. That is, as indicated by an arrowhead in FIG. 7C, the hair follicle germ on day 7 of culture had a hair shaft-like structure formed therein.

Example 5

[Collection of Epithelial Cells and Mesenchymal Cells]

Epithelial cells and mesenchymal cells were prepared in the same manner as in Example 1 described above.

[Culture]

In example 5-1, the epithelial cells and the mesenchymal cells were co-cultured using a culture solution containing laminin. That is, first, DMEM/F12 medium containing 1% GultaMax Supplement and 0.2% Normocin was prepared as the culture solution.

Then, the epithelial cells and the mesenchymal cells in such amounts as to achieve a cell density of $5 \times 10^3$ cells/mL each (such amounts as to achieve a total cell density of $1 \times 10^4$ cells/mL) were suspended in the culture solution, and a high-purity laminin product (LAMININ-ULTRAPURE, MOUSE, CORNING (trademark)) in such an amount as to achieve a concentration of 1 v/v % was further added to prepare a cell suspension.

The high-purity laminin product used contained 0.82 mg/mL of a soluble basement membrane matrix extracted from an EHS mouse tumor, and contained laminin at a purity of 95% or more according to SDS-PAGE.

Accordingly, it is calculated that the cell suspension having 1 v/v % of the high-purity laminin product added thereto contained about 8 µg/mL of laminin. That is, it is calculated that, in the cell suspension of example 5-1, the content of laminin was from 13% to 14% of that in the cell suspension of example 1-1 of Example 1 described above.

100 µL of the cell suspension was placed in each well of a 96-well plate to inoculate the epithelial cells and the mesenchymal cells. Immediately after the inoculation, the 96-well plate was transferred into a refrigerator at 4° C. and left at rest for 20 minutes. As a result, the epithelial cells and the mesenchymal cells were sedimented on the bottom surface of each well in the cooled culture solution in the refrigerator.

After that, the 96-well plate was transferred to an incubator at 37° C., and co-culture of the epithelial cells and the mesenchymal cells was started in the incubator. The culture solution was changed in the same manner as in example 1-1 of Example 1 described above.

In example 5-2, the epithelial cells and the mesenchymal cells were co-cultured using a culture solution containing laminin and entactin in the same manner as in example 4 of Example 4 described above.

In example 5-3, the epithelial cells and the mesenchymal cells were co-cultured using a culture solution containing type IV collagen. That is, first, DMEM/F12 medium containing 1% GultaMax Supplement and 0.2% Normocin was prepared as the culture solution.

Then, the epithelial cells and the mesenchymal cells in such amounts as to achieve a cell density of $5 \times 10^3$ cells/mL each (such amounts as to achieve a total cell density of $1 \times 10^4$ cells/mL) were suspended in the culture solution, and a type IV collagen product (COLLAGEN IV, MOUSE, CORNING (trademark)) in such an amount as to achieve a concentration of 1 v/v % was further added to prepare a cell suspension.

The type IV collagen product used contained 1.25 mg/mL of a soluble basement membrane matrix extracted from an EHS mouse tumor, and contained type IV collagen at a purity of 90% or more according to SDS-PAGE.

Accordingly, it is calculated that the cell suspension having 1 v/v % of the type IV collagen product added thereto contained 11 μg/mL to 13 μg/mL of type IV collagen. That is, in the cell suspension of example 5-3, the content of type IV collagen was from 34% to 38% of that in the cell suspension of example 1-1 of Example 1 described above.

100 μL of the cell suspension was placed in each well of a 96-well plate to inoculate the epithelial cells and the mesenchymal cells. Immediately after the inoculation, the 96-well plate was transferred into a refrigerator at 4° C. and left at rest for 20 minutes. As a result, the cells were sedimented on the bottom surface of each well in the cooled culture solution in the refrigerator.

After that, the 96-well plate was transferred to an incubator at 37° C., and co-culture of the epithelial cells and the mesenchymal cells was started in the incubator. The culture solution was changed in the same manner as in example 1-1 of Example 1 described above.

[Results]

Figure 8A:
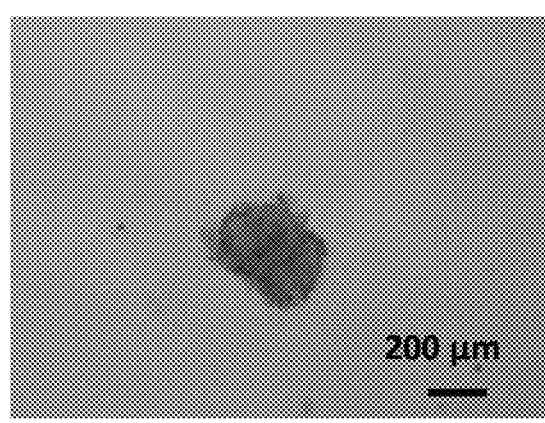
FIG. 8A is an explanatory diagram showing an example of a phase-contrast micrograph taken on day 8 of culture in example 5-1 according to one embodiment of the present invention.
Figure 8B:
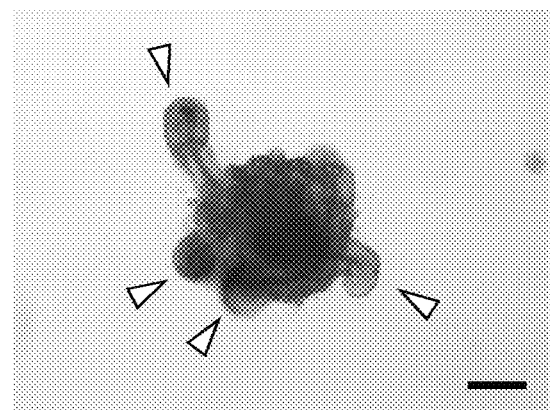
FIG. 8B is an explanatory diagram showing an example of a phase-contrast micrograph taken on day 8 of culture in example 5-2 according to one embodiment of the present invention.
Figure 8C:
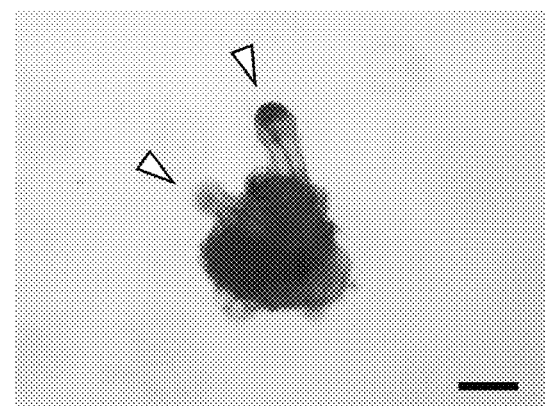
FIG. 8C is an explanatory diagram showing an example of a phase-contrast micrograph taken on day 8 of culture in example 5-3 according to one embodiment of the present invention.

FIG. 8A, FIG. 8B, and FIG. 8C show phase-contrast micrographs taken on day 8 of culture in example 5-1, example 5-2, and example 5-3, respectively. In each of FIG. 8A to FIG. 8C, the scale bar represents 200 μm.

As shown in FIG. 8A, in example 5-1 using the culture solution containing laminin, the hair follicle germ on day 8 of culture had no hair shaft-like structure formed therein. In contrast, as indicated by arrowheads in FIG. 8B, in example 5-2 using the culture solution containing laminin and entactin, the hair follicle germ on day 8 of culture had hair shaft-like structures formed therein. In addition, as indicated by arrowheads in FIG. 8C, also in example 5-3 using the culture solution containing type IV collagen, the hair follicle germ on day 8 of culture had hair shaft-like structures formed therein.

Example 6

[Collection of Epithelial Cells and Mesenchymal Cells]

Epithelial cells and mesenchymal cells were prepared in the same manner as in Example 1 described above.

[Culture]

In example 6, the epithelial cells and the mesenchymal cells were co-cultured for 8 days in the same manner as in example 1-1 of Example 1 described above except that a Matrigel product having a reduced content of growth factors (Matrigel (trademark) Basement Membrane Matrix (Growth Factor Reduced), CORNING (trademark)) was used in such an amount as to achieve a concentration of 1 v/v % in the culture solution in place of the Matrigel product used in example 1-1 of Example 1.

The Matrigel product (GFR) used contained 8 mg/mL to 12 mg/mL (protein amount measured by the Lowry method) of a soluble basement membrane matrix extracted from an Engelbreth-Holm-Swarm (EHS) mouse tumor, and a compositional ratio in the basement membrane matrix was as follows: 61% of laminin, 7% of entactin, and 30% of type IV collagen.

[Results]

Figure 9A:
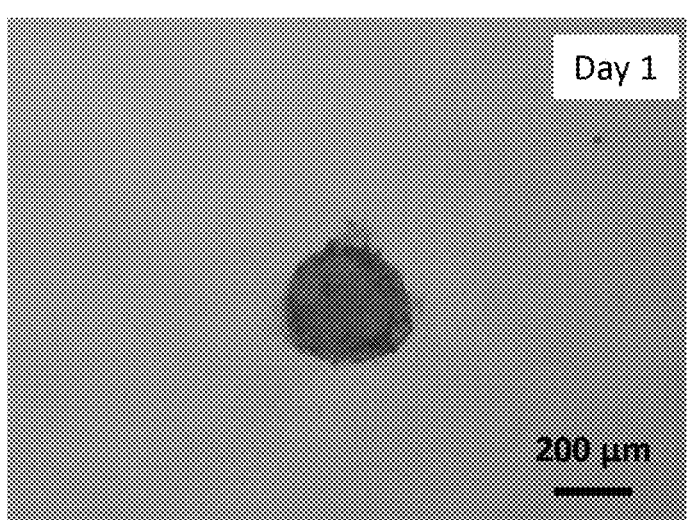
FIG. 9A is an explanatory diagram showing an example of a phase-contrast micrograph taken on day 1 of culture in example 6 according to one embodiment of the present invention.
Figure 9B:
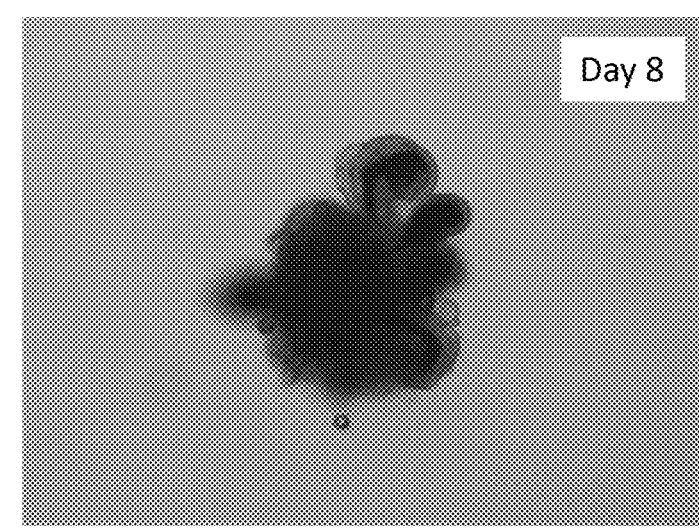
FIG. 9B is an explanatory diagram showing an example of a phase-contrast micrograph taken on day 8 of culture in example 6 according to one embodiment of the present invention.
Figure 10A:
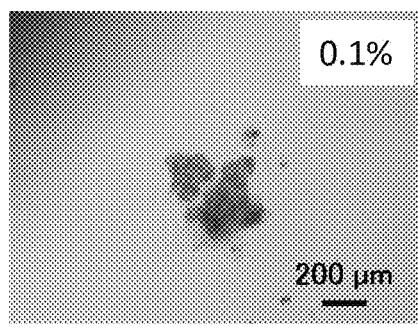
FIG. 10A is an explanatory diagram showing an example of a phase-contrast micrograph taken on day 1 of culture in example 7-1 according to one embodiment of the present invention.
Figure 10B:
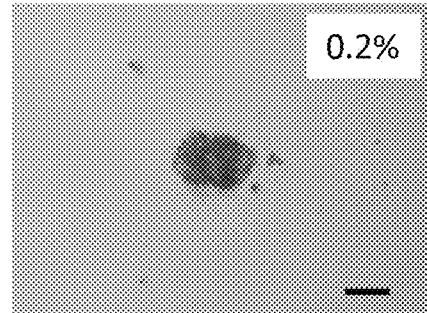
FIG. 10B is an explanatory diagram showing an example of a phase-contrast micrograph taken on day 1 of culture in example 7-2 according to one embodiment of the present invention.
Figure 10C:
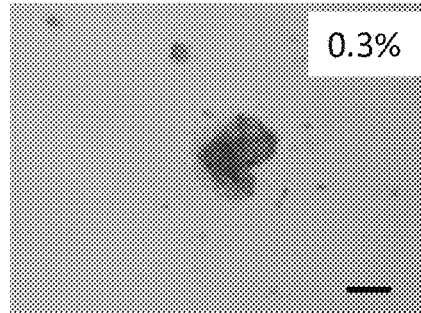
FIG. 10C is an explanatory diagram showing an example of a phase-contrast micrograph taken on day 1 of culture in example 7-3 according to one embodiment of the present invention.
Figure 10D:
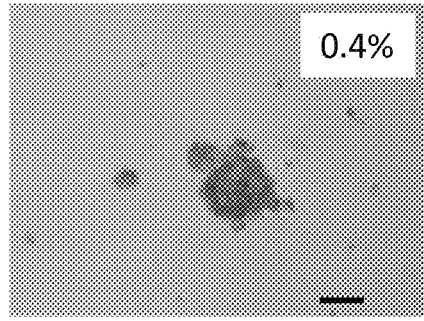
FIG. 10D is an explanatory diagram showing an example of a phase-contrast micrograph taken on day 1 of culture in example 7-4 according to one embodiment of the present invention.
Figure 10E:
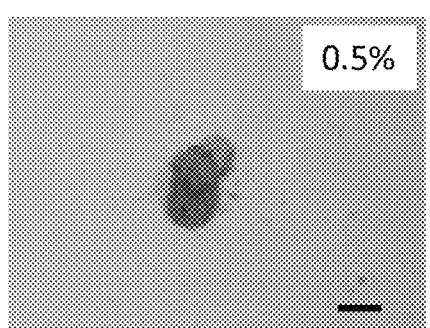
FIG. 10E is an explanatory diagram showing an example of a phase-contrast micrograph taken on day 1 of culture in example 7-5 according to one embodiment of the present invention.
Figure 10F:
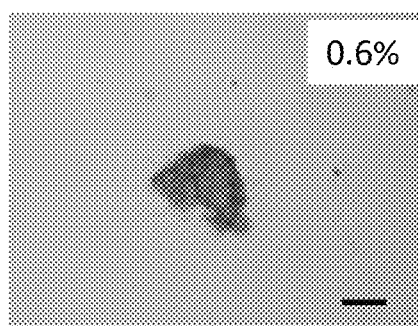
FIG. 10F is an explanatory diagram showing an example of a phase-contrast micrograph taken on day 1 of culture in example 7-6 according to one embodiment of the present invention.
Figure 11A:
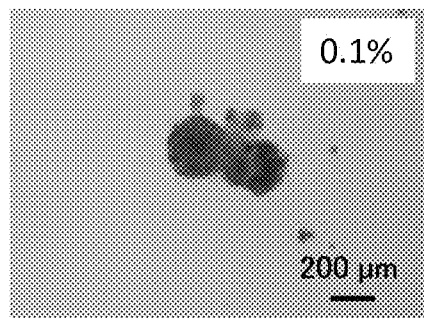
FIG. 11A is an explanatory diagram showing an example of a phase-contrast micrograph taken on day 3 of culture in example 7-1 according to one embodiment of the present invention.
Figure 11B:
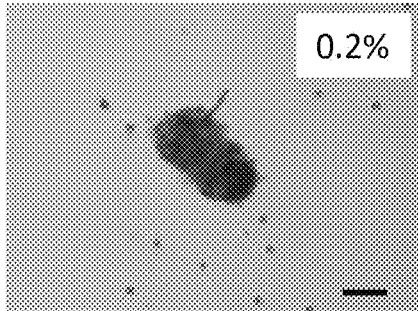
FIG. 11B is an explanatory diagram showing an example of a phase-contrast micrograph taken on day 3 of culture in example 7-2 according to one embodiment of the present invention.
Figure 11C:
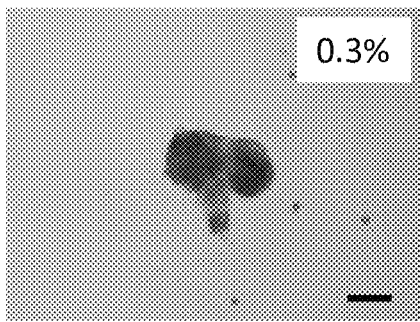
FIG. 11C is an explanatory diagram showing an example of a phase-contrast micrograph taken on day 3 of culture in example 7-3 according to one embodiment of the present invention.
Figure 11D:
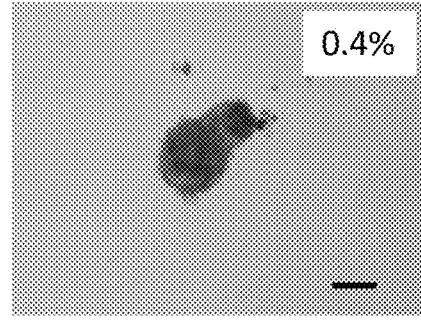
FIG. 11D is an explanatory diagram showing an example of a phase-contrast micrograph taken on day 3 of culture in example 7-4 according to one embodiment of the present invention.
Figure 11E:
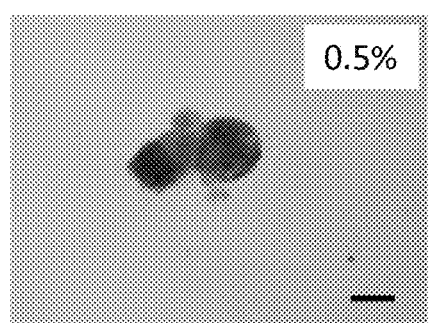
FIG. 11E is an explanatory diagram showing an example of a phase-contrast micrograph taken on day 3 of culture in example 7-5 according to one embodiment of the present invention.
Figure 11F:
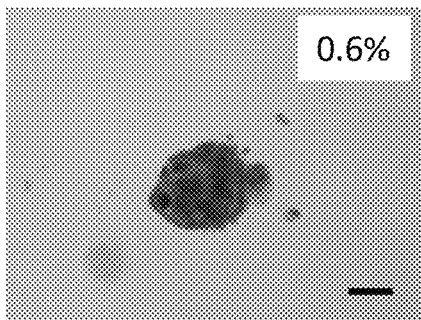
FIG. 11F is an explanatory diagram showing an example of a phase-contrast micrograph taken on day 3 of culture in example 7-6 according to one embodiment of the present invention.
Figure 12A:
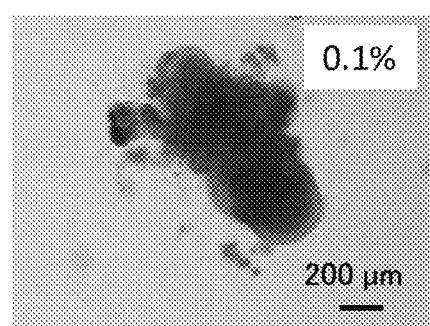
FIG. 12A is an explanatory diagram showing an example of a phase-contrast micrograph taken on day 8 of culture in example 7-1 according to one embodiment of the present invention.
Figure 12B:
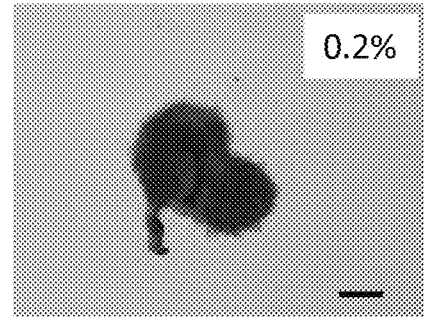
FIG. 12B is an explanatory diagram showing an example of a phase-contrast micrograph taken on day 8 of culture in example 7-2 according to one embodiment of the present invention.
Figure 12C:
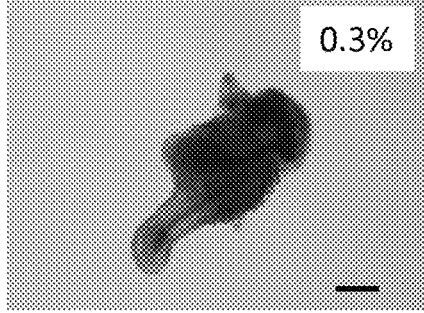
FIG. 12C is an explanatory diagram showing an example of a phase-contrast micrograph taken on day 8 of culture in example 7-3 according to one embodiment of the present invention.
Figure 12D:
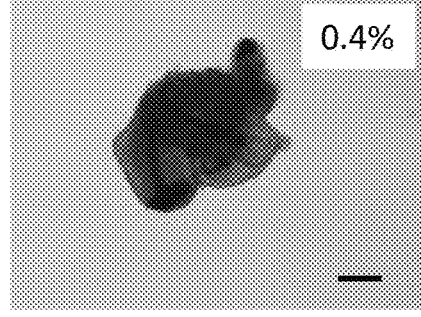
FIG. 12D is an explanatory diagram showing an example of a phase-contrast micrograph taken on day 8 of culture in example 7-4 according to one embodiment of the present invention.
Figure 12E:
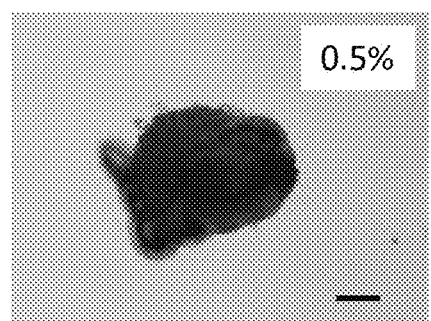
FIG. 12E is an explanatory diagram showing an example of a phase-contrast micrograph taken on day 8 of culture in example 7-5 according to one embodiment of the present invention.
Figure 12F:
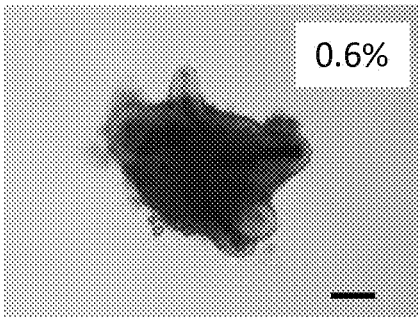
FIG. 12F is an explanatory diagram showing an example of a phase-contrast micrograph taken on day 8 of culture in example 7-6 according to one embodiment of the present invention.
Figure 13A:
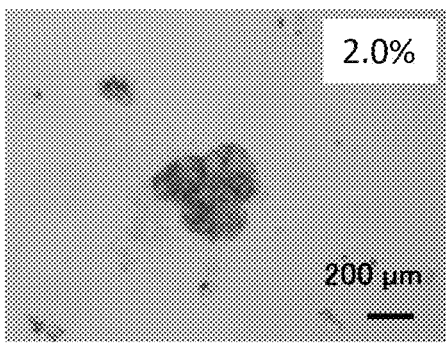
FIG. 13A is an explanatory diagram showing an example of a phase-contrast micrograph taken on day 1 of culture in example 8-1 according to one embodiment of the present invention.
Figure 13B:
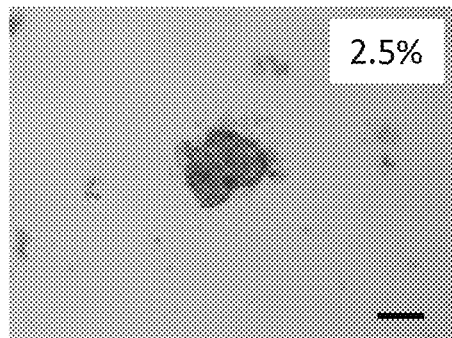
FIG. 13B is an explanatory diagram showing an example of a phase-contrast micrograph taken on day 1 of culture in example 8-2 according to one embodiment of the present invention.
Figure 13C:
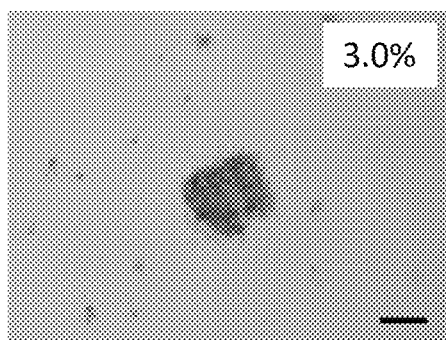
FIG. 13C is an explanatory diagram showing an example of a phase-contrast micrograph taken on day 1 of culture in example 8-3 according to one embodiment of the present invention.
Figure 13D:
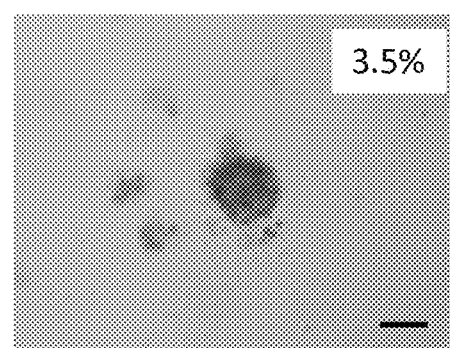
FIG. 13D is an explanatory diagram showing an example of a phase-contrast micrograph taken on day 1 of culture in example 8-4 according to one embodiment of the present invention.
Figure 13E:
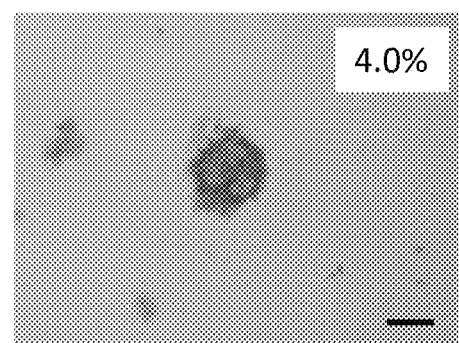
FIG. 13E is an explanatory diagram showing an example of a phase-contrast micrograph taken on day 1 of culture in example 8-5 according to one embodiment of the present invention.
Figure 13F:
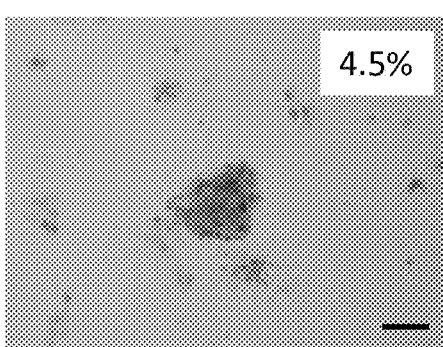
FIG. 13F is an explanatory diagram showing an example of a phase-contrast micrograph taken on day 1 of culture in example 8-6 according to one embodiment of the present invention.
Figure 14A:
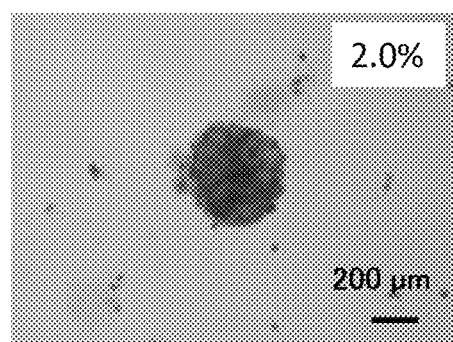
FIG. 14A is an explanatory diagram showing an example of a phase-contrast micrograph taken on day 3 of culture in example 8-1 according to one embodiment of the present invention.
Figure 14B:
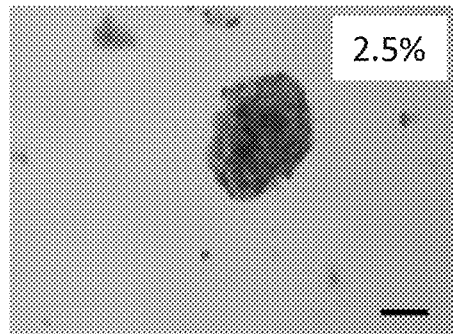
FIG. 14B is an explanatory diagram showing an example of a phase-contrast micrograph taken on day 3 of culture in example 8-2 according to one embodiment of the present invention.
Figure 14C:
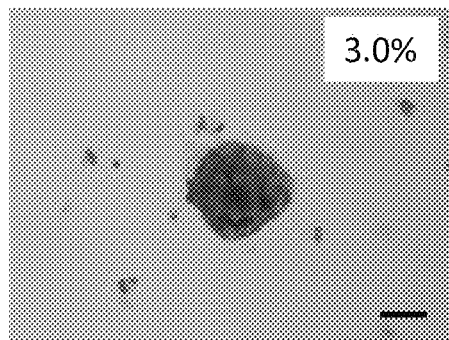
FIG. 14C is an explanatory diagram showing an example of a phase-contrast micrograph taken on day 3 of culture in example 8-3 according to one embodiment of the present invention.
Figure 14D:
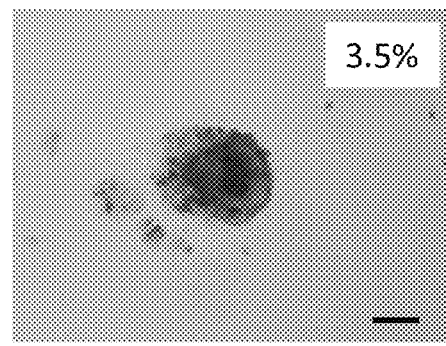
FIG. 14D is an explanatory diagram showing an example of a phase-contrast micrograph taken on day 3 of culture in example 8-4 according to one embodiment of the present invention.
Figure 14E:
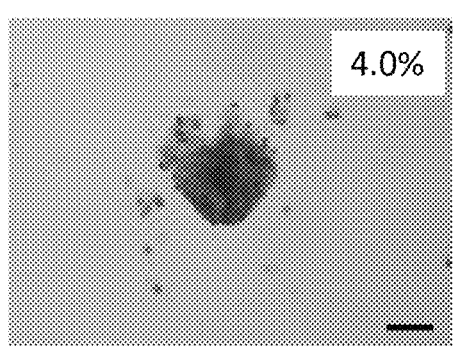
FIG. 14E is an explanatory diagram showing an example of a phase-contrast micrograph taken on day 3 of culture in example 8-5 according to one embodiment of the present invention.
Figure 14F:
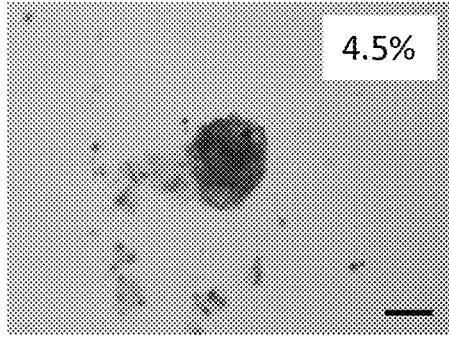
FIG. 14F is an explanatory diagram showing an example of a phase-contrast micrograph taken on day 3 of culture in example 8-6 according to one embodiment of the present invention.
Figure 15A:
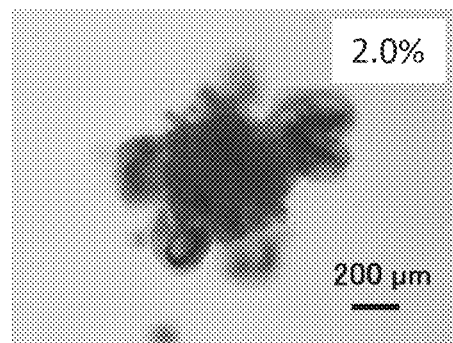
FIG. 15A is an explanatory diagram showing an example of a phase-contrast micrograph taken on day 8 of culture in example 8-1 according to one embodiment of the present invention.
Figure 15B:
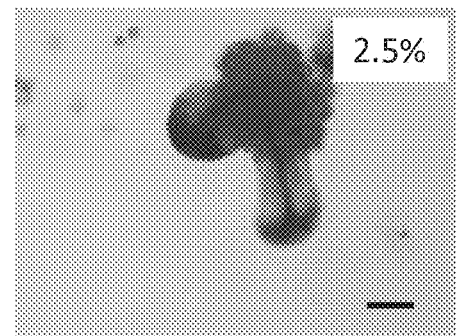
FIG. 15B is an explanatory diagram showing an example of a phase-contrast micrograph taken on day 8 of culture in example 8-2 according to one embodiment of the present invention.
Figure 15C:
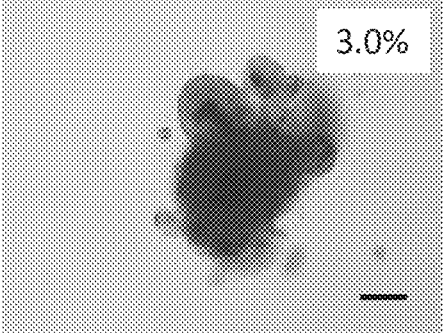
FIG. 15C is an explanatory diagram showing an example of a phase-contrast micrograph taken on day 8 of culture in example 8-3 according to one embodiment of the present invention.
Figure 15D:
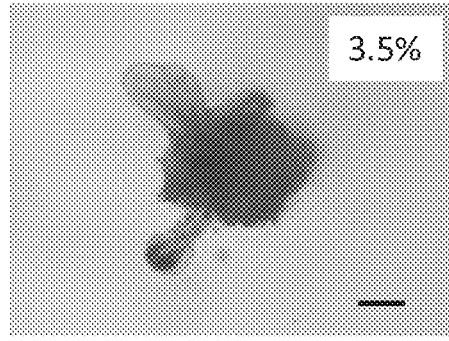
FIG. 15D is an explanatory diagram showing an example of a phase-contrast micrograph taken on day 8 of culture in example 8-4 according to one embodiment of the present invention.
Figure 15E:
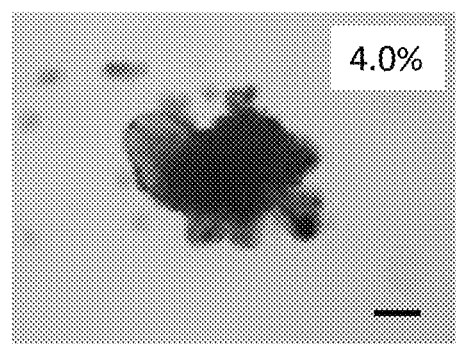
FIG. 15E is an explanatory diagram showing an example of a phase-contrast micrograph taken on day 8 of culture in example 8-5 according to one embodiment of the present invention.
Figure 15F:
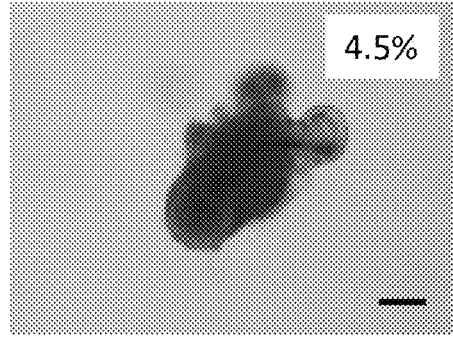
FIG. 15F is an explanatory diagram showing an example of a phase-contrast micrograph taken on day 8 of culture in example 8-6 according to one embodiment of the present invention.

FIG. 9A and FIG. 9B show phase-contrast micrographs taken on day 1 of culture and day 8 of culture, respectively, in the co-culture of example 6. As shown in FIG. 9A and FIG. 9B, in example 6, a hair follicle germ having hair shaft-like structures was formed. That is, as shown in FIG. 9B, the hair follicle germ on day 8 of culture had hair shaft-like structures formed therein.

In addition, the formation of a hair shaft-like structure was recognized in 85 hair follicle germs out of the 96 hair follicle germs, and hence the hair shaft-like structure formation ratio was 89%. That is, in example 6, hair follicle germs having hair shaft-like structures were formed as in example 1-1 described above, and the hair shaft-like structure formation ratio were also comparable to that of example 1-1.

Example 7

[Collection of Epithelial Cells and Mesenchymal Cells]

Epithelial cells and mesenchymal cells were prepared in the same manner as in Example 1 described above.

[Culture]

In example 7-1, the epithelial cells and the mesenchymal cells were co-cultured in the same manner as in example 1-1 of Example 1 described above except that the concentration of Matrigel added to the culture solution was changed from 1 v/v % to 0.1 v/v %. It is calculated that the cell suspension having 0.1 v/v % of Matrigel added thereto contained 6 μg/mL of laminin, 1 μg/mL of entactin, and 3 μg/mL of type IV collagen.

In example 7-2, the epithelial cells and the mesenchymal cells were co-cultured in the same manner as in example 1-1 of Example 1 described above except that the concentration of Matrigel added to the culture solution was changed from 1 v/v % to 0.2 v/v %. It is calculated that the cell suspension having 0.2 v/v % of Matrigel added thereto contained 12 μg/mL of laminin, 2 μg/mL of entactin, and 7 μg/mL of type IV collagen.

In example 7-3, the epithelial cells and the mesenchymal cells were co-cultured in the same manner as in example 1-1 of Example 1 described above except that the concentration of Matrigel added to the culture solution was changed from 1 v/v % to 0.3 v/v %. It is calculated that the cell suspension having 0.3 v/v % of Matrigel added thereto contained 18 μg/mL of laminin, 3 μg/mL of entactin, and 10 μg/mL of type IV collagen.

In example 7-4, the epithelial cells and the mesenchymal cells were co-cultured in the same manner as in example 1-1 of Example 1 described above except that the concentration of Matrigel added to the culture solution was changed from 1 v/v % to 0.4 v/v %. It is calculated that the cell suspension having 0.4 v/v % of Matrigel added thereto contained 24 μg/mL of laminin, 3 μg/mL of entactin, and 13 μg/mL of type IV collagen.

In example 7-5, the epithelial cells and the mesenchymal cells were co-cultured in the same manner as in example 1-1 of Example 1 described above except that the concentration of Matrigel added to the culture solution was changed from 1 v/v % to 0.5 v/v %. It is calculated that the cell suspension having 0.5 v/v % of Matrigel added thereto contained 30 μg/mL of laminin, 4 μg/mL of entactin, and 16 μg/mL of type IV collagen.

In example 7-6, the epithelial cells and the mesenchymal cells were co-cultured in the same manner as in example 1-1 of Example 1 described above except that the concentration of Matrigel added to the culture solution was changed from 1 v/v % to 0.6 v/v %. It is calculated that the cell suspension having 0.6 v/v % of Matrigel added thereto contained 36 μg/mL of laminin, 5 μg/mL of entactin, and 20 μg/mL of type IV collagen.

[Results]

FIG. 10A, FIG. 10B, FIG. 10C, FIG. 10D, FIG. 10E, and FIG. 10F show phase-contrast micrographs taken on day 1 of culture in the co-culture of example 7-1, example 7-2, example 7-3, example 7-4, example 7-5, and example 7-6, respectively. FIG. 11A, FIG. 11B, FIG. 11C, FIG. 11D, FIG. 11E, and FIG. 11F show phase-contrast micrographs taken on day 3 of culture in the co-culture of example 7-1, example 7-2, example 7-3, example 7-4, example 7-5, and example 7-6, respectively. FIG. 12A, FIG. 12B, FIG. 12C, FIG. 12D, FIG. 12E, and FIG. 12F show phase-contrast micrographs taken on day 8 of culture in the co-culture of example 7-1, example 7-2, example 7-3, example 7-4, example 7-5, and example 7-6, respectively. In each of FIG. 10A to FIG. 10F, FIG. 11A to FIG. 11F, and FIG. 12A to FIG. 12F, the scale bar represents 200 μm.

As shown in FIG. 10A to FIG. 10F, FIG. 11A to FIG. 11F, and FIG. 12A to FIG. 12F, in all of the examples (example 7-1 to example 7-6), a hair follicle germ having a hair shaft-like structure was formed. That is, as shown in FIG. 12A to FIG. 12F, in all the examples, the hair follicle germ on day 8 of culture had a hair shaft-like structure formed therein.

In addition, the hair shaft-like structure formation ratios on day 8 of culture were: 25% (3 out of 12 hair follicle germs) in example 7-1; 58% (7 out of 12 hair follicle germs) in example 7-2; 92% (11 out of 12 hair follicle germs) in example 7-3; and 100% (12 out of 12 hair follicle germs) in example 7-4, example 7-5, and example 7-6.

Example 8

[Collection of Epithelial Cells and Mesenchymal Cells]

Epithelial cells and mesenchymal cells were prepared in the same manner as in Example 1 described above.

[Culture]

In example 8-1, the epithelial cells and the mesenchymal cells were co-cultured in the same manner as in example 1-1 of Example 1 described above except that the concentration of Matrigel added to the culture solution was changed from 1 v/v % to 2.0 v/v %. It is calculated that the cell suspension having 2.0 v/v % of Matrigel added thereto contained 119 μg/mL of laminin, 17 μg/mL of entactin, and 66 μg/mL of type IV collagen.

In example 8-2, the epithelial cells and the mesenchymal cells were co-cultured in the same manner as in example 1-1 of Example 1 described above except that the concentration of Matrigel added to the culture solution was changed from 1 v/v % to 2.5 v/v %. It is calculated that the cell suspension having 2.5 v/v % of Matrigel added thereto contained 148 μg/mL of laminin, 21 μg/mL of entactin, and 82 μg/mL of type IV collagen.

In example 8-3, the epithelial cells and the mesenchymal cells were co-cultured in the same manner as in example 1-1 of Example 1 described above except that the concentration of Matrigel added to the culture solution was changed from 1 v/v % to 3.0 v/v %. It is calculated that the cell suspension having 3.0 v/v % of Matrigel added thereto contained 178 μg/mL of laminin, 25 μg/mL of entactin, and 99 μg/mL of type IV collagen.

In example 8-4, the epithelial cells and the mesenchymal cells were co-cultured in the same manner as in example 1-1 of Example 1 described above except that the concentration of Matrigel added to the culture solution was changed from 1 v/v % to 3.5 v/v %. It is calculated that the cell suspension having 3.5 v/v % of Matrigel added thereto contained 208 μg/mL of laminin, 30 μg/mL of entactin, and 115 μg/mL of type IV collagen.

In example 8-5, the epithelial cells and the mesenchymal cells were co-cultured in the same manner as in example 1-1 of Example 1 described above except that the concentration of Matrigel added to the culture solution was changed from 1 v/v % to 4.0 v/v %. It is calculated that the cell suspension having 4.0 v/v % of Matrigel added thereto contained 237 μg/mL of laminin, 34 μg/mL of entactin, and 131 μg/mL of type IV collagen.

In example 8-6, the epithelial cells and the mesenchymal cells were co-cultured in the same manner as in example 1-1 of Example 1 described above except that the concentration of Matrigel added to the culture solution was changed from 1 v/v % to 4.5 v/v %. The cell suspension having 4.5 v/v % of Matrigel added thereto contained 267 μg/mL of laminin, 38 μg/mL of entactin, and 148 μg/mL of type IV collagen.

[Results]

FIG. 13A, FIG. 13B, FIG. 13C, FIG. 13D, FIG. 13E, and FIG. 13F show phase-contrast micrographs taken on day 1 of culture in the co-culture of example 8-1, example 8-2, example 8-3, example 8-4, example 8-5, and example 8-6, respectively. FIG. 14A, FIG. 14B, FIG. 14C, FIG. 14D, FIG. 14E, and FIG. 14F show phase-contrast micrographs taken on day 3 of culture in the co-culture of example 8-1, example 8-2, example 8-3, example 8-4, example 8-5, and example 8-6, respectively. FIG. 15A, FIG. 15B, FIG. 15C, FIG. 15D, FIG. 15E, and FIG. 15F show phase-contrast micrographs taken on day 8 of culture in the co-culture of example 8-1, example 8-2, example 8-3, example 8-4, example 8-5, and example 8-6, respectively. In each of FIG. 13A to FIG. 13F, FIG. 14A to FIG. 14F, and FIG. 15A to FIG. 15F, the scale bar represents 200 μm.

As shown in FIG. 13A to FIG. 13F, FIG. 14A to FIG. 14F, and FIG. 15A to FIG. 15F, in all of the examples (example 8-1 to example 8-6), a hair follicle germ having a hair shaft-like structure was formed. That is, as shown in FIG. 15A to FIG. 15F, in all the examples, the hair follicle germ on day 8 of culture had a hair shaft-like structure formed therein.

In addition, the hair shaft-like structure formation ratios on day 8 of culture were: 100% (6 out of 6 hair follicle germs) in example 8-1, example 8-2, and example 8-3; and 100% (12 out of 12 hair follicle germs) also in example 8-4, example 8-5, and example 8-6.

Example 9

[Collection of Epithelial Cells and Mesenchymal Cells]

Epithelial cells and mesenchymal cells were prepared in the same manner as in Example 1 described above.

[Culture]

In example 9-1, the epithelial cells and the mesenchymal cells were co-cultured in the same manner as in example 4 of Example 4 described above except that the concentration of the high concentration laminin/entactin complex product added to the culture solution was changed from 1 v/v % to 0.5 v/v %. It is calculated that the cell suspension having 0.5 v/v % of the high concentration laminin/entactin complex product added thereto contained 68 µg/mL to 76 µg/mL of the laminin/entactin complex (i.e., 34 µg/mL to 38 µg/mL each of laminin and entactin).

In example 9-2, the epithelial cells and the mesenchymal cells were co-cultured in the same manner as in example 4 of Example 4 described above except that the concentration of the high concentration laminin/entactin complex product added to the culture solution was changed from 1 v/v % to 5.0 v/v %. It is calculated that the cell suspension having 5.0 v/v % of the high concentration laminin/entactin complex product added thereto contained 684 µg/mL to 760 µg/mL of the laminin/entactin complex (i.e., 342 µg/mL to 380 µg/mL each of laminin and entactin).

In example 9-3, the epithelial cells and the mesenchymal cells were co-cultured in the same manner as in example 4 of Example 4 described above except that the concentration of the high concentration laminin/entactin complex product added to the culture solution was changed from 1 v/v % to 10.0 v/v %. It is calculated that the cell suspension having 10.0 v/v % of the high concentration laminin/entactin complex product added thereto contained 1,368 µg/mL to 1,520 µg/mL of the laminin/entactin complex (i.e., 684 µg/mL to 760 µg/mL each of laminin and entactin).

[Results]

Figure 16A:
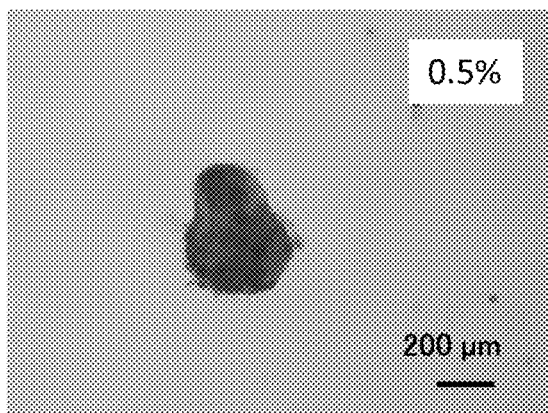
FIG. 16A is an explanatory diagram showing an example of a phase-contrast micrograph taken on day 2 of culture in example 9-1 according to one embodiment of the present invention.
Figure 16B:
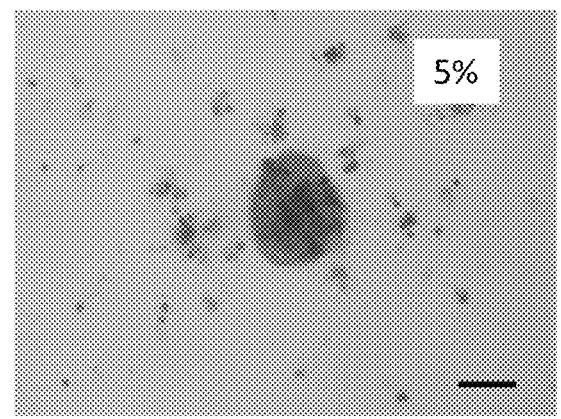
FIG. 16B is an explanatory diagram showing an example of a phase-contrast micrograph taken on day 2 of culture in example 9-2 according to one embodiment of the present invention.
Figure 16C:
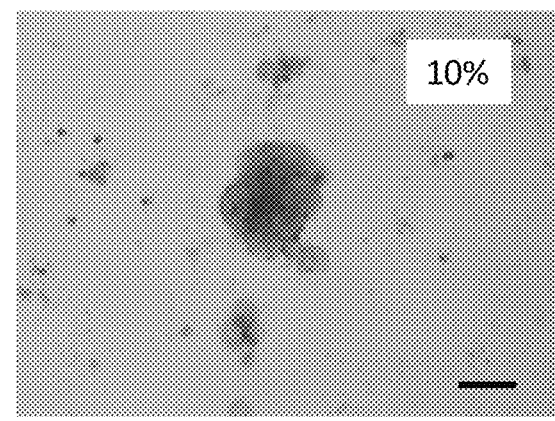
FIG. 16C is an explanatory diagram showing an example of a phase-contrast micrograph taken on day 2 of culture in example 9-3 according to one embodiment of the present invention.
Figure 17A:
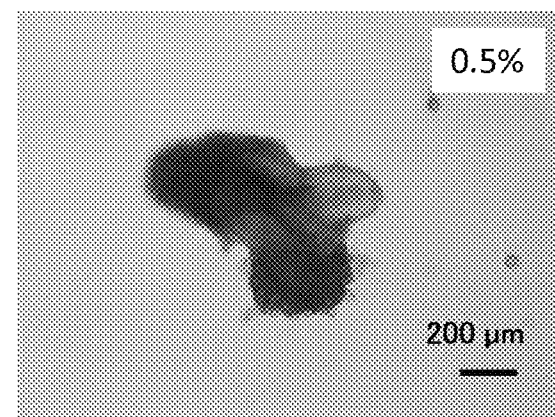
FIG. 17A is an explanatory diagram showing an example of a phase-contrast micrograph taken on day 8 of culture in example 9-1 according to one embodiment of the present invention.
Figure 17B:
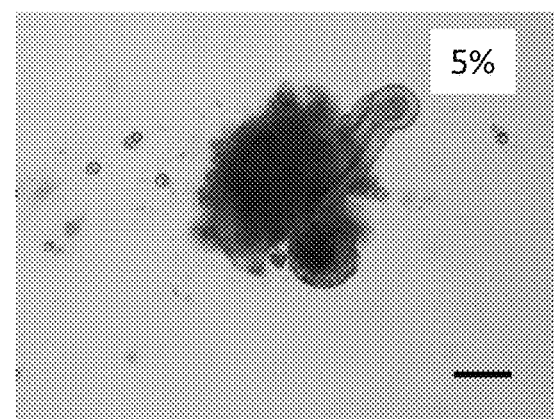
FIG. 17B is an explanatory diagram showing an example of a phase-contrast micrograph taken on day 8 of culture in example 9-2 according to one embodiment of the present invention.
Figure 17C:
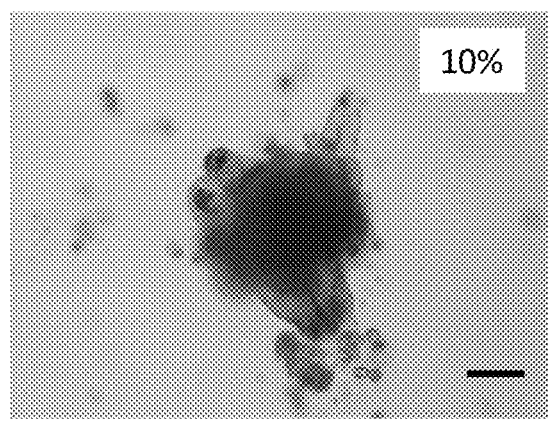
FIG. 17C is an explanatory diagram showing an example of a phase-contrast micrograph taken on day 8 of culture in example 9-3 according to one embodiment of the present invention.

FIG. 16A, FIG. 16B, and FIG. 16C show phase-contrast micrographs taken on day 2 of culture in the co-culture of example 9-1, example 9-2, and example 9-3, respectively. FIG. 17A, FIG. 17B, and FIG. 17C show phase-contrast micrographs taken on day 8 of culture in the co-culture of example 9-1, example 9-2, and example 9-3, respectively. In each of FIG. 16A to FIG. 16C, and FIG. 17A to FIG. 17C, the scale bar represents 200 µm.

As shown in FIG. 16A to FIG. 16C, and FIG. 17A to FIG. 17C, in all of the examples (example 9-1 to example 9-3), a hair follicle germ having a hair shaft-like structure was formed. That is, as shown in FIG. 17A to FIG. 17C, in all the examples, the hair follicle germ on day 8 of culture had a hair shaft-like structure formed therein.

Reference Example 1

[Collection of Epithelial Cells and Mesenchymal Cells]

Epithelial cells and mesenchymal cells were prepared in the same manner as in Example 1 described above.

[Culture]

In example C1-1, the epithelial cells and the mesenchymal cells were co-cultured in the same manner as in example 4 of Example 4 described above except that the concentration of the high-purity laminin product added to the culture solution was changed from 1 v/v % to 5 v/v %. It is calculated that the cell suspension containing 5 v/v % of the high-purity laminin product contained 39 µg/mL to 41 µg/mL of laminin.

In example C1-2, the epithelial cells and the mesenchymal cells were co-cultured in the same manner as in example 4 of Example 4 described above except that the concentration of the high-purity laminin product added to the culture solution was changed from 1 v/v % to 10 v/v %. It is calculated that the cell suspension containing 10 v/v % of the high-purity laminin product contained 78 µg/mL to 82 µg/mL of laminin.

[Results]

Figure 18A:
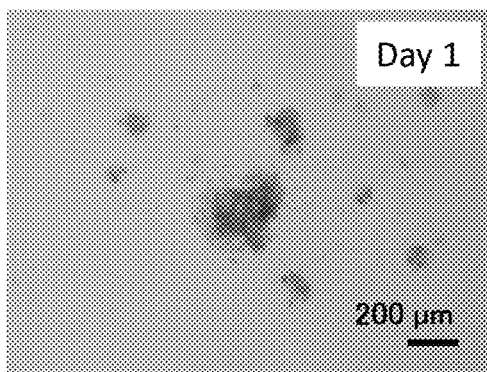
FIG. 18A is an explanatory diagram showing an example of a phase-contrast micrograph taken on day 1 of culture in example C1-1 according to one embodiment of the present invention.
Figure 18B:
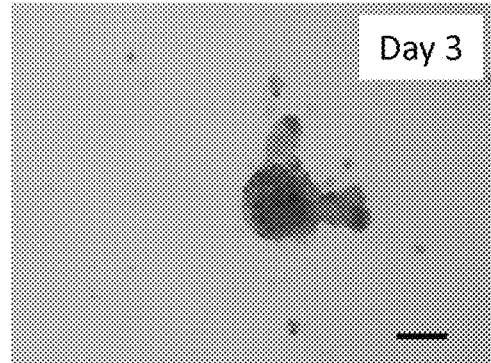
FIG. 18B is an explanatory diagram showing an example of a phase-contrast micrograph taken on day 3 of culture in example C1-1 according to one embodiment of the present invention.
Figure 18C:
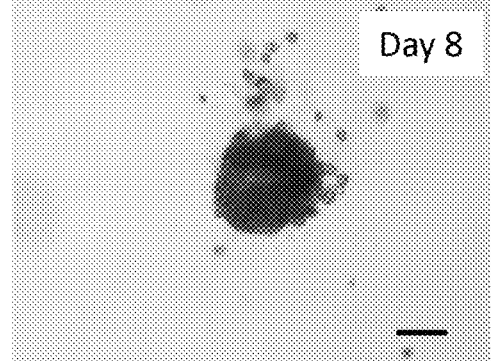
FIG. 18C is an explanatory diagram showing an example of a phase-contrast micrograph taken on day 8 of culture in example C1-1 according to one embodiment of the present invention.
Figure 18D:
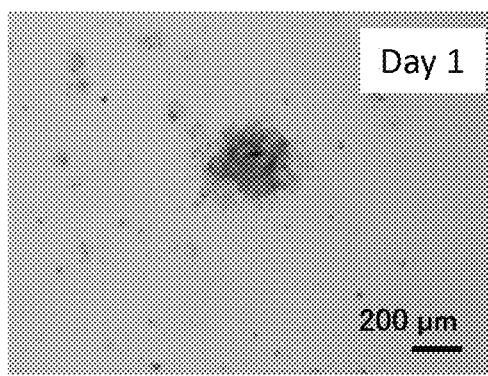
FIG. 18D is an explanatory diagram showing an example of a phase-contrast micrograph taken on day 1 of culture in example C1-2 according to one embodiment of the present invention.
Figure 18E:
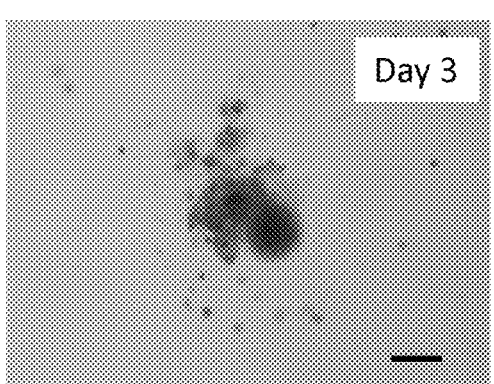
FIG. 18E is an explanatory diagram showing an example of a phase-contrast micrograph taken on day 3 of culture in example C1-2 according to one embodiment of the present invention.
Figure 18F:
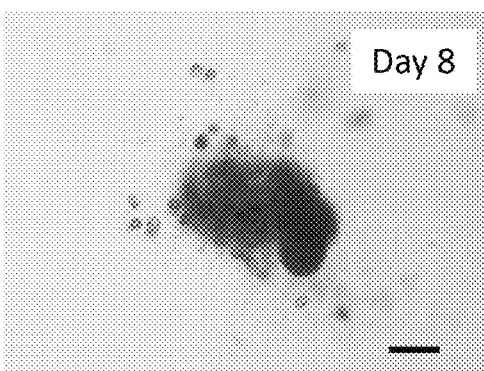
FIG. 18F is an explanatory diagram showing an example of a phase-contrast micrograph taken on day 8 of culture in example C1-2 according to one embodiment of the present invention.

FIG. 18A, FIG. 18B, and FIG. 18C show phase-contrast micrographs taken on day 1 of culture, day 3 of culture, and day 8 of culture, respectively, in the co-culture of example C1-1. FIG. 18D, FIG. 18E, and FIG. 18F show phase-contrast micrographs taken on day 1 of culture, day 3 of culture, and day 8 of culture, respectively, in the co-culture of example C1-2. In each of FIG. 18A to FIG. 18F, the scale bar represents 200 µm.

As shown in FIG. 18A to FIG. 18F, a hair follicle germ having a hair shaft-like structure was not formed in any of example C1-1 and example C1-2.

Reference Example 2

[Collection of Epithelial Cells and Mesenchymal Cells]

Epithelial cells and mesenchymal cells were prepared in the same manner as in Example 1 described above.

[Culture]

In example C2, the epithelial cells and the mesenchymal cells were co-cultured in a culture solution free of type IV collagen on a culture dish surface coated in advance with type IV collagen. First, the type IV collagen product used in example 5-3 of Example 5 described above was diluted to a concentration of 100 µg/mL with a 0.05 M HCl solution in accordance with a description concerning a coating method in the instruction manual of the product to prepare a coating liquid. Then, 1 mL of the coating liquid was added to culture dishes each having a diameter of 35 mm, and was kept at room temperature for 1 hour. After that, the coating liquid was discarded from the culture dishes, and the surfaces of the culture dishes were washed with purified water.

Meanwhile, the epithelial cells and the mesenchymal cells in such amounts as to achieve a cell density of $5 \times 10^3$ cells/mL each (such amounts as to achieve a total cell density of $1 \times 10^4$ cells/mL) were suspended in DMEM/F12 medium containing 1% GultaMax Supplement and 0.2% Normocin to prepare a cell suspension.

2 mL of the cell suspension was placed in each of the culture dishes coated in advance with type IV collagen as described above. Thus, the epithelial cells and the mesenchymal cells were inoculated, and co-culture was started.

[Results]

Figure 19A:
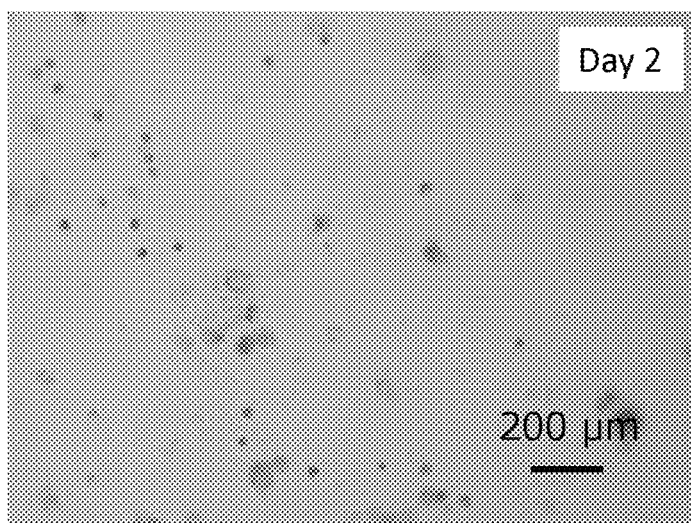
FIG. 19A is an explanatory diagram showing an example of a phase-contrast micrograph taken on day 2 of culture in example C2 according to one embodiment of the present invention.
Figure 19B:
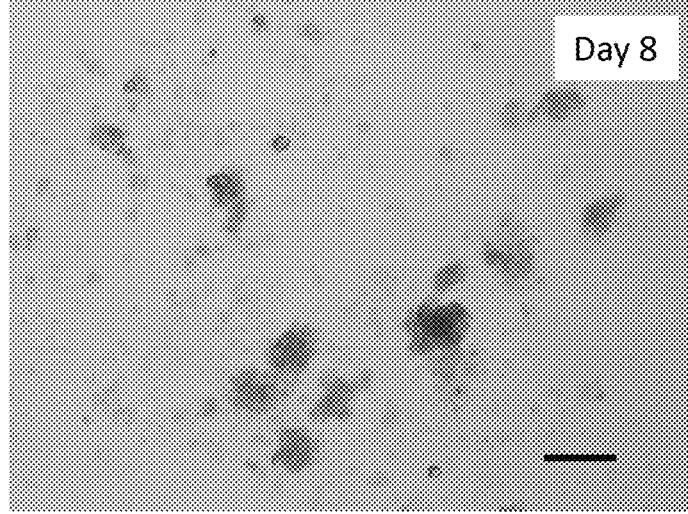
FIG. 19B is an explanatory diagram showing an example of a phase-contrast micrograph taken on day 8 of culture in example C2 according to one embodiment of the present invention.
Figure 20A:
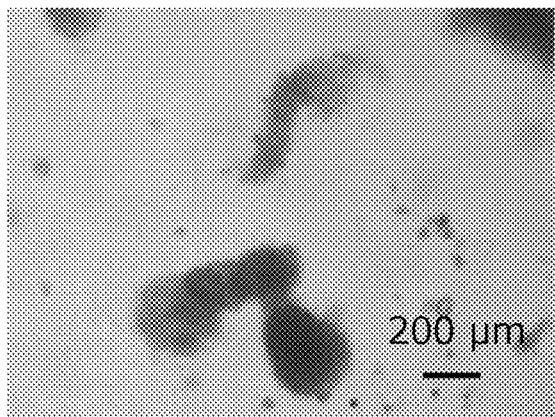
FIG. 20A is an explanatory diagram showing an example of a phase-contrast micrograph taken on day 12 of culture in example C3-1 according to one embodiment of the present invention.
Figure 20B:
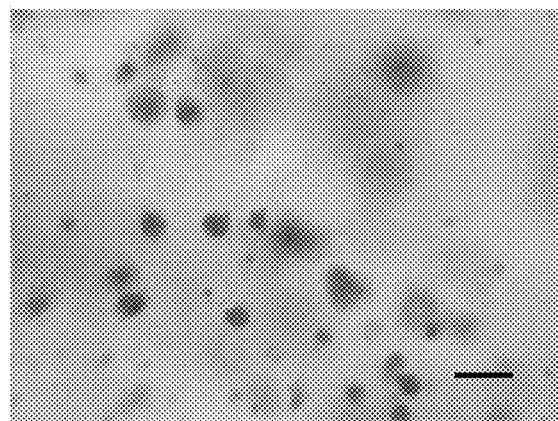
FIG. 20B is an explanatory diagram showing an example of a phase-contrast micrograph taken on day 12 of culture in example C3-2 according to one embodiment of the present invention.
Figure 20C:
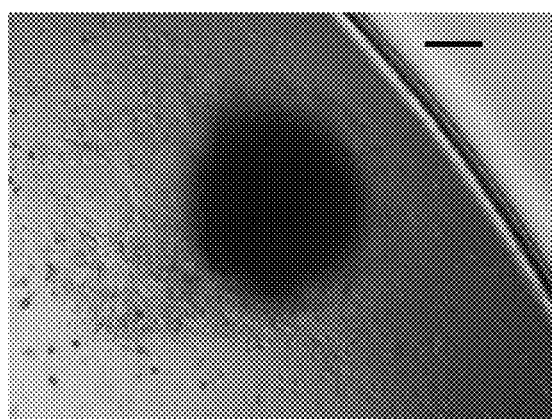
FIG. 20C is an explanatory diagram showing an example of a phase-contrast micrograph taken on day 12 of culture in example C3-3 according to one embodiment of the present invention.
Figure 20D:
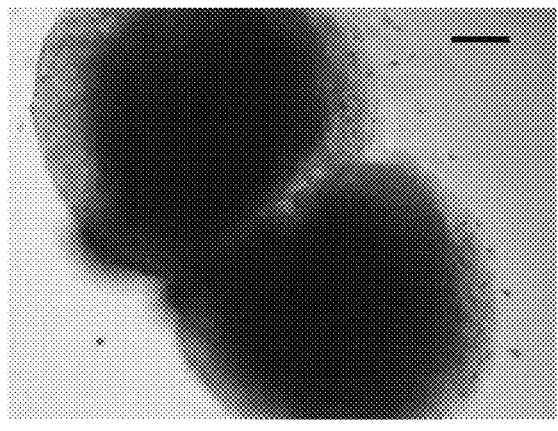
FIG. 20D is an explanatory diagram showing an example of a phase-contrast micrograph taken on day 12 of culture in example C3-4 according to one embodiment of the present invention.

FIG. 19A and FIG. 19B show phase-contrast micrographs taken on day 2 of culture and day 8 of culture, respectively, in the co-culture of example C2. In each of FIG. 19A and FIG. 19B, the scale bar represents 200 µm.

As shown in FIG. 19A and FIG. 19B, when the epithelial cells and the mesenchymal cells were co-cultured in the culture solution free of type IV collagen on the culture dish surface subjected to coating treatment with type IV collagen, a hair follicle germ having a hair shaft-like structure was not formed.

Reference Example 3

[Collection of Epithelial Cells and Mesenchymal Cells]

Epithelial cells and mesenchymal cells were prepared in the same manner as in Example 1 described above.

[Culture]

In example C3-1, the epithelial cells and the mesenchymal cells were co-cultured on a gel containing laminin, entactin, and type IV collagen in a culture solution free of laminin, entactin, and type IV collagen.

That is, first, 50 µL of the Matrigel product used in example 1-1 of Example 1 described above was dropped onto the bottom surface of each well of a 96-well flat-bottom culture plate, and was incubated at 37° C. for 15 minutes to gelate. After that, the epithelial cells and the mesenchymal cells suspended in a culture solution free of the Matrigel product were inoculated on the gel in each well, and co-cultured on the gel.

In example C3-2, the epithelial cells and the mesenchymal cells were co-cultured in a gel containing laminin, entactin, and type IV collagen.

That is, first, the Matrigel product was mixed with the epithelial cells and the mesenchymal cells, and 50 μL of the resultant cell suspension was dropped onto the bottom surface of each well of a 96-well flat-bottom culture plate, and was incubated at 37° C. for 15 minutes to gelate. After that, a culture solution free of the Matrigel product was poured on the gel, in which the dispersed epithelial cells and mesenchymal cells were embedded, in each well, and co-culture was performed in the gel.

In example C3-3, a hair follicle germ formed by co-culturing the epithelial cells and the mesenchymal cells in a culture solution free of laminin, entactin, and type IV collagen was cultured on a gel containing laminin, entactin, and type IV collagen in a culture solution free of laminin, entactin, and type IV collagen.

That is, first, in the same manner as in example 1-2 of Example 1 described above, the epithelial cells and the mesenchymal cells were co-cultured for 3 days in a culture solution free of laminin, entactin, and type IV collagen to form a hair follicle germ containing the epithelial cells and the mesenchymal cells.

Meanwhile, a gel of Matrigel was formed in the same manner as in example C3-1 described above. Then, the hair follicle germ formed as described above was inoculated on the gel formed as described above in a culture solution not having added thereto Matrigel, and the hair follicle germ was cultured on the gel for 9 days.

In example C3-4, a hair follicle germ formed by co-culturing the epithelial cells and the mesenchymal cells in a culture solution free of laminin, entactin, and type IV collagen was cultured in a gel containing laminin, entactin, and type IV collagen.

That is, first, in the same manner as in example 1-2 of Example 1 described above, the epithelial cells and the mesenchymal cells were co-cultured for 3 days in a culture solution free of laminin, entactin, and type IV collagen to form a hair follicle germ containing the epithelial cells and the mesenchymal cells. Then, in the same manner as in example C3-2 described above, the hair follicle germ was embedded in a gel of Matrigel, and the hair follicle germ was cultured in the gel for 9 days.

[Results]

FIG. 20A, FIG. 20B, FIG. 20C, and FIG. 20D show phase-contrast micrographs taken on day 12 of culture in example C3-1, example C3-2, example C3-3, and example C3-4, respectively. In each of FIG. 20A to FIG. 20D, the scale bar represents 200 μm.

As shown in FIG. 20A to FIG. 20D, a hair follicle germ having a hair shaft-like structure was not formed in any of example C3-1 to example C3-4.

Example 10

[Collection of Epithelial Cells and Mesenchymal Cells]

Epithelial cells and mesenchymal cells were prepared in the same manner as in Example 1 described above.

[Culture]

In example 10, the epithelial cells and the mesenchymal cells were co-cultured using a culture solution containing laminin, entactin, and type IV collagen. First, DMEM/F12 medium containing 1% GultaMax Supplement and 0.2% Normocin was prepared as the culture solution.

Then, the epithelial cells and the mesenchymal cells in such amounts as to achieve a cell density of $5 \times 10^3$ cells/200

μL each (such amounts as to achieve a total cell density of $1 \times 10^4$ cells/200 μL) were suspended in the culture solution, and Matrigel in such an amount as to achieve a concentration of 1 v/v % was further added to prepare a cell suspension.

200 μL of the cell suspension was placed in each well of a 96-well plate to inoculate the epithelial cells and the mesenchymal cells. Immediately after the inoculation, the 96-well plate was transferred into a refrigerator at 4° C. and left at rest for 20 minutes. As a result of being left at rest, the epithelial cells and the mesenchymal cells were sedimented on the bottom surface of each well in a state of being allowed to be brought into contact with each other in the cooled culture solution in the refrigerator. After that, the 96-well plate was transferred to an incubator at 37° C., and co-culture of the epithelial cells and the mesenchymal cells was started in the incubator. The co-culture was performed for 6 days.

In the co-culture, the culture solution was changed once every 2 days. The culture solution was changed by first removing 100 μL of the culture solution from each well, and then adding 100 μL of DMEM/F12 medium free of Matrigel and containing 1% GultaMax Supplement and 0.2% Normocin to each well as a fresh culture solution.

[Transplantation of Hair Follicle Germs]

Hair follicle germs formed by the 6 days of co-culture were observed under a phase-contrast microscope to determine whether or not each of the hair follicle germs had a hair shaft-like structure formed therein. Then, only hair follicle germs each having a hair shaft-like structure formed therein were selectively collected, and transplanted under the skin of a 5-week-old ICR nude mouse (Oriental Yeast Co., Ltd.) under anesthesia using an isoflurane anesthesia machine for small animals (Bio Research Center Co., Ltd.). That is, punctures for transplantation were formed in the dorsal part of the nude mouse using an ophthalmic V-lance (20G, Alcon Japan Ltd.), and 21 hair follicle germs each having a hair shaft-like structure were inserted into the punctures for transplantation through use of a pipette.

[Results]

Figure 21:
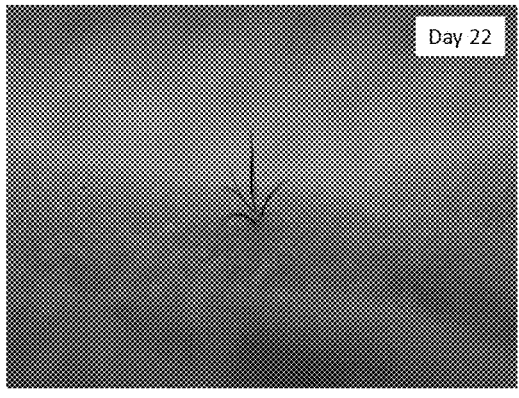
FIG. 21 is an explanatory diagram showing an example of a state in which hair has been regenerated from a hair follicle germ transplanted to the dorsal part of a nude mouse in example 10 according to one embodiment of the present invention.

FIG. 21 shows an example of a photograph of the dorsal part of the nude mouse on day 22 after the transplantation. As shown in FIG. 21, hair was formed at a site in the dorsal part of the nude mouse at which a hair follicle germ was transplanted. Specifically, the formation of hair was recognized from 18 out of the 21 transplanted hair follicle germs. That is, the ratio of the number of hair follicle germs that formed hair in the dorsal part of the nude mouse where the hair follicle germs were transplanted to the total number of transplanted hair follicle germs (hair regeneration efficiency) was 85.7% (=$^{18}/_{21} \times 100$). The hair regeneration efficiency was higher than that in the case where hair follicle germs having no hair shaft-like structure, which were formed using a culture solution free of laminin, entactin, and type IV collagen, were transplanted (the result is not shown in the drawings). Thus, it was recognized that hair was regenerated with high efficiency by transplanting the hair follicle germs produced through the co-culture described above to a living body.

Example 11

[Collection of Epithelial Cells and Mesenchymal Cells]

Epithelial cells and mesenchymal cells were prepared in the same manner as in Example 1 described above. However, first, the mesenchymal cells were collected from a first mouse individual on the day only the mesenchymal cells were inoculated, and then the epithelial cells were collected from a second mouse individual different from the first individual on the day the epithelial cells were further inoculated, which was after 1 day of culture of the mesenchymal cells.

[Culture]

In example 11, first, culture of only the mesenchymal cells was started using a culture solution containing laminin, entactin, and type IV collagen. Then, the epithelial cells were added, and co-culture of the epithelial cells and the mesenchymal cells was performed using a culture solution containing laminin, entactin, and type IV collagen.

DMEM/F12 medium containing 1% GultaMax Supplement and 0.2% Normocin was prepared as the culture solution. The mesenchymal cells in such an amount as to achieve a cell density of $5\times10^4$ cells/mL were suspended in the culture solution, and Matrigel in such an amount as to achieve a concentration of 1 v/v % was further added to prepare a cell suspension of the mesenchymal cells.

100 µL of the cell suspension of the mesenchymal cells was placed in each well of a 96-well plate to inoculate the mesenchymal cells (cell density of mesenchymal cells: $5\times10^3$ cells/well). Immediately after the inoculation, the 96-well plate was transferred into a refrigerator at 4° C. and left at rest for 20 minutes to cause the mesenchymal cells to be sedimented on the bottom surface of each well. After that, the 96-well plate was transferred to an incubator at 37° C., and culture of the mesenchymal cells was started in the incubator. The culture of the mesenchymal cells was performed for 1 day.

After 1 day from the start of the culture of the mesenchymal cells, the epithelial cells in such an amount as to achieve a cell density of $5\times10^4$ cells/mL were suspended in a culture solution (DMEM/F12 medium containing 1% GultaMax Supplement and 0.2% Normocin), and Matrigel in such an amount as to achieve a concentration of 1 v/v % was further added to prepare a suspension of the epithelial cells.

Meanwhile, the 96-well plate containing the mesenchymal cells cultured for 1 day as described above was transferred into a refrigerator at 4° C. and left at rest for 20 minutes. After that, 100 µL of the suspension of the epithelial cells was placed in each well containing the mesenchymal cells to inoculate the epithelial cells (cell density of epithelial cells: $5\times10^3$ cells/well).

After the inoculation of the epithelial cells, the 96-well plate containing the epithelial cells and the mesenchymal cells was transferred into a refrigerator at 4° C. and left at rest for 20 minutes. After that, the 96-well plate was transferred to an incubator at 37° C., and co-culture of the epithelial cells and the mesenchymal cells was started in the incubator. The co-culture was performed for 14 days. That is, the co-culture of the epithelial cells and the mesenchymal cells was performed for 14 days from the day the epithelial cells were inoculated in each well containing the mesenchymal cells. The culture solution was changed in the same manner as in example 10 described above.

[Results]

Figure 22A:
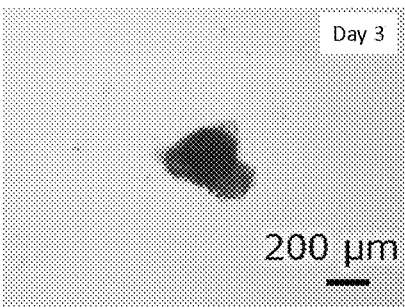
FIG. 22A is an explanatory diagram showing an example of a phase-contrast micrograph taken on day 3 of culture in example 11 according to one embodiment of the present invention.
Figure 22B:
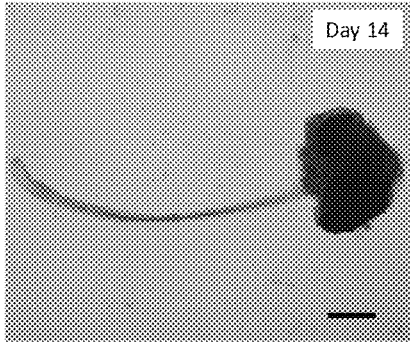
FIG. 22B is an explanatory diagram showing an example of a phase-contrast micrograph taken on day 14 of culture in example 11 according to one embodiment of the present invention.

FIG. 22A and FIG. 22B show phase-contrast micrographs taken on day 3 and day 14 from the start of co-culture, respectively, in the co-culture of example 11. In each of FIG. 22A and FIG. 22B, the scale bar represents 200 µm.

As shown in FIG. 22A, many of the hair follicle germs that had been formed by day 3 of culture contained a mesenchymal cell aggregate formed through aggregation of the mesenchymal cells, and an epithelial cell aggregate formed through aggregation of the epithelial cells and serially combined to the mesenchymal cell aggregate. In addition, as shown in FIG. 22B, it was recognized on day 14 of culture that one long hair shaft-like structure was formed from one hair follicle germ.

Figure 23:
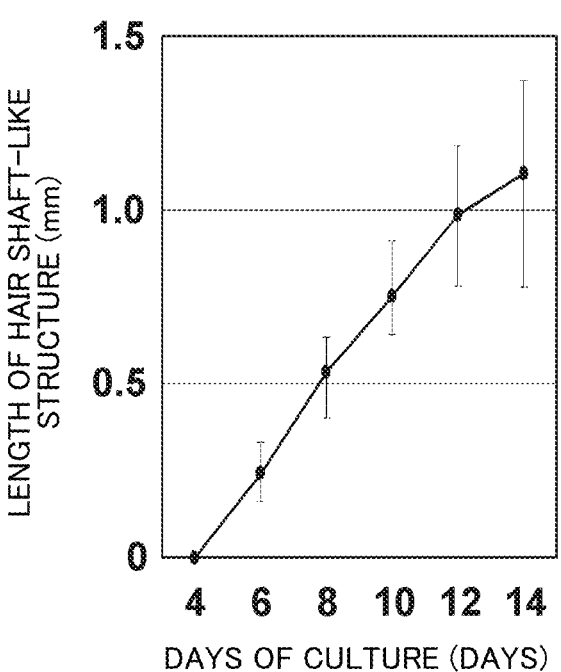
FIG. 23 is an explanatory diagram showing an example of the results of measurement of the length of hair shaft-like structures formed in hair follicle germs during co-culture in example 11 according to one embodiment of the present invention.

FIG. 23 shows the results of measurement of the length of hair shaft-like structures formed in hair follicle germs during co-culture. In FIG. 23, the horizontal axis represents the number of days of co-culture, and the vertical axis represents the length of hair shaft-like structures formed in hair follicle germs.

As shown in FIG. 23, hair shaft-like structures started to be observed after a lapse of 4 days from the start of co-culture, and then the hair shaft-like structures grew and elongated with the lapse of culture time.

Figure 24A:
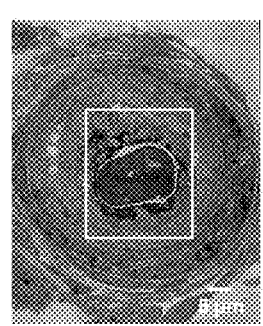
FIG. 24A is an explanatory diagram showing an example of a transmission micrograph obtained by photographing a cross-section of a hair shaft-like structure formed in a hair follicle germ on day 14 of culture in example 11 according to one embodiment of the present invention.
Figure 24B:
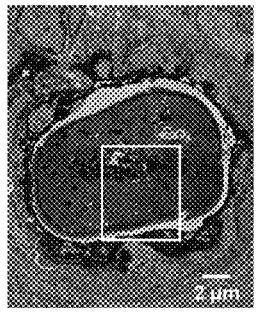
FIG. 24B is an explanatory diagram showing an enlarged image of the rectangular area surrounded by a white line shown in FIG. 24A.
Figure 24C:
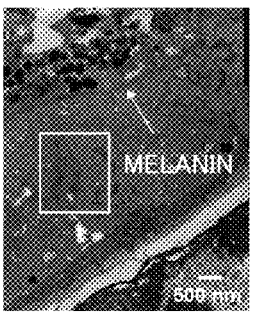
FIG. 24C is an explanatory diagram showing an enlarged image of the rectangular area surrounded by a white line shown in FIG. 24B.
Figure 24D:
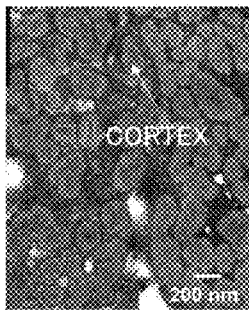
FIG. 24D is an explanatory diagram showing an enlarged image of the rectangular area surrounded by a white line shown in FIG. 24C.

FIG. 24A shows a photograph obtained by observing, with a transmission microscope, a cross-section of a hair shaft-like structure formed in a hair follicle germ on day 14 of culture. In FIG. 24A, the scale bar represents 5 µm. FIG. 24B shows an enlarged image of the rectangular area surrounded by a white line shown in FIG. 24A. In FIG. 24B, the scale bar represents 2 µm. FIG. 24C shows an enlarged image of the rectangular area surrounded by a white line shown in FIG. 24B. In FIG. 24C, the scale bar represents 500 nm. FIG. 24D shows an enlarged image of the rectangular area surrounded by a white line shown in FIG. 24C. In FIG. 24D, the scale bar represents 200 nm.

As shown in FIG. 24A to FIG. 24D, it was recognized that the hair shaft-like structure formed in the hair follicle germ had structures similar to those of the hair of a living body, such as melanin and cortex.

Example 12

[Collection of Epithelial Cells and Mesenchymal Cells]

A dorsal skin tissue was collected from a Bulb/c mouse embryo at embryonic day 18, and was subjected to dispase treatment by a partially modified version of a method reported by Nakao et al. (Koh-ei Toyoshima et al. Nature Communications, 3, 784, 2012) at 4° C. under the shaking condition of 30 rpm for 1 hour to separate the epithelial layer and mesenchymal layer of the skin tissue. After that, the epithelial layer was treated with 100 U/mL collagenase for 1 hour and 20 minutes and further treated with trypsin for 10 minutes to isolate epithelial cells. In addition, the mesenchymal layer was treated with 100 U/mL collagenase for 1 hour and 20 minutes to isolate mesenchymal cells.

[Culture]

In example 12-1, the epithelial cells, the mesenchymal cells, and melanocytes were co-cultured using a culture solution containing laminin, entactin, and type IV collagen. First, DMEM/F12 medium containing 1% GultaMax Supplement and 0.2% Normocin was prepared as the culture solution.

Then, the epithelial cells and the mesenchymal cells in such amounts as to achieve a cell density of $5\times10^3$ cells/200 µL each, and melanocytes (normal human (black) epidermal melanocytes) in such an amount as to achieve a cell density of $1.25\times10^3$ cells/200 µL were suspended in the culture solution (total cell density: $1.125\times10^4$ cells/200 µL), and Matrigel in such an amount as to achieve a concentration of 1 v/v % was further added to prepare a cell suspension.

200 µL of the cell suspension was placed in each well of a 96-well plate to inoculate the epithelial cells, the mesenchymal cells, and the melanocytes. Immediately after the inoculation, the 96-well plate was transferred into a refrigerator at 4° C. and left at rest for 20 minutes. As a result of being left at rest, the epithelial cells, the mesenchymal cells, and the melanocytes were sedimented on the bottom surface of each well in a state of being allowed to be brought into contact with each other. After that, the 96-well plate was transferred to an incubator at 37° C., and co-culture of the epithelial cells, the mesenchymal cells, and the melanocytes was started in the incubator. The co-culture was performed for 8 days. The culture solution was changed in the same manner as in example 10 described above.

In example 12-2, the epithelial cells, the mesenchymal cells, and the melanocytes were co-cultured in the same manner as in example 12-1 described above except that the melanocytes were used in such an amount as to achieve a cell density of $2.5 \times 10^3$ cells/200 µL (total cell density: $1.25 \times 10^4$ cells/200 µL).

In example 12-3, the epithelial cells, the mesenchymal cells, and the melanocytes were co-cultured in the same manner as in example 12-1 described above except that the melanocytes were used in such an amount as to achieve a cell density of $5 \times 10^3$ cells/200 µL (total cell density: $1.5 \times 10^4$ cells/200 µL).

In example 12-C1, the epithelial cells and the mesenchymal cells were co-cultured in the same manner as in example 12-1 described above except that the melanocytes were not used (total cell density: $1 \times 10^4$ cells/200 µL).

That is, ratios among the numbers of the three kinds of cells inoculated (epithelial cells:mesenchymal cells:melanocytes) were "1:1:0" in example 12-C1, "4:4:1" in example 12-1, "2:2:1" in example 12-2, and "1:1:1" in example 12-3.

[Results]

FIG. 25A, FIG. 25B, FIG. 25C, and FIG. 25D show phase-contrast micrographs taken on day 8 of culture in the co-culture of example 12-1, example 12-2, and example 12-3, respectively.

Figure 25A:
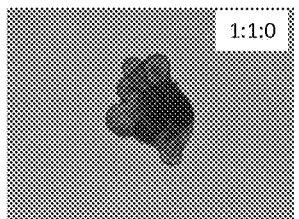
FIG. 25A is an explanatory diagram showing an example of a phase-contrast micrograph taken on day 8 of culture in example 12-C1 according to one embodiment of the present invention.
Figure 25B:
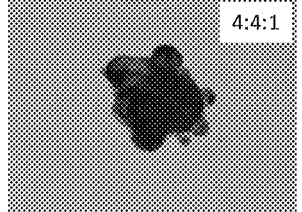
FIG. 25B is an explanatory diagram showing an example of a phase-contrast micrograph taken on day 8 of culture in example 12-1 according to one embodiment of the present invention.
Figure 25C:
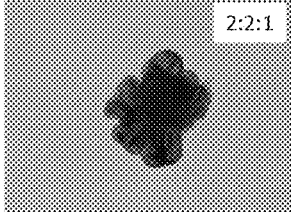
FIG. 25C is an explanatory diagram showing an example of a phase-contrast micrograph taken on day 8 of culture in example 12-2 according to one embodiment of the present invention.
Figure 25D:
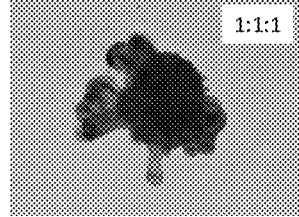
FIG. 25D is an explanatory diagram showing an example of a phase-contrast micrograph taken on day 8 of culture in example 12-3 according to one embodiment of the present invention.

As shown in FIG. 25A, a hair follicle germ having white hair shaft-like structures was formed through co-culture of the epithelial cells and the mesenchymal cells derived from the Bulb/c mouse having white hair. In contrast, as shown in FIG. 25B to FIG. 25D, in all of example 12-1 to example 12-3, a hair follicle germ having black hair shaft-like structures was formed through co-culture further including the melanocytes in addition to the epithelial cells and the mesenchymal cells derived from the Bulb/c mouse having white hair.

The invention claimed is:

1. A method of producing a hair follicle germ, comprising:
inoculating epithelial cells and mesenchymal cells;
contacting the epithelial cells and the mesenchymal cells, before a hair follicle germ containing the epithelial cells and the mesenchymal cells is formed, with a first culture solution having fluidity at a temperature of 30° C. or more and 45° C. or less and comprising (a) laminin and entactin, and/or (b) type IV collagen; and
co-culturing the epithelial cells and the mesenchymal cells in a second culture solution to form the hair follicle germ,
wherein the contacting is performed before 28 hours have passed from a time point when the co-culturing is started, and
wherein the epithelial cells and the mesenchymal cells are inoculated in a culture solution in which the (a) and/or the (b) is dispersed; or a culture solution in which the (a) and/or the (b) is not dispersed.

2. The method of producing a hair follicle germ according to claim 1, wherein the first culture solution comprises (a) laminin and entactin.

3. The method of producing a hair follicle germ according to claim 1, wherein the first culture solution comprises (b) type IV collagen.

4. The method of producing a hair follicle germ according to claim 1, further comprising causing the inoculated epithelial cells and mesenchymal cells to be sedimented on a culture substrate,
wherein the method comprises maintaining the epithelial cells and the mesenchymal cells sedimented on the culture substrate in the first culture solution.

5. The method of producing a hair follicle germ according to claim 1, wherein the method comprises, after maintaining the epithelial cells and the mesenchymal cells in the first culture solution in which the (a) and/or the (b) is dispersed, co-culturing the epithelial cells and the mesenchymal cells in the second culture solution in which a concentration of the (a) and/or the (b) is lower than that in the first culture solution.

6. The method of producing a hair follicle germ according to claim 1,
wherein the method further comprises forming the hair follicle germ having a hair shaft-like structure in-vitro by the co-culture, and
wherein the hair shaft-like structure is a structure containing keratin and having a string shape with a length of 30 µm or more.

7. A method of promoting formation of a hair shaft-like structure in a hair follicle germ in vitro, the method comprising
producing the hair follicle germ according to the method of claim 1,
wherein the hair shaft-like structure is a structure containing keratin and having a string shape with a length of 30 µm or more.

8. A method of using (a) laminin and entactin, and/or (b) type IV collagen for promoting formation of a hair shaft-like structure in a hair follicle germ in vitro, the method comprising
producing the hair follicle germ according to the method of claim 1,
wherein the hair shaft-like structure is a structure containing keratin and having a string shape with a length of 30 µm or more.

9. The method of producing a hair follicle germ according to claim 1,
wherein a concentration of the (a) and/or the (b) in the first culture solution is lower than a concentration for causing gelation of the entire culture solution.

10. The method of producing a hair follicle germ according to claim 1,
wherein a concentration of the (a) laminin and entactin in the first culture solution is 1 µg/mL or more.

11. The method of producing a hair follicle germ according to claim 10, wherein a concentration of the (a) laminin and entactin in the first culture solution is 1 µg/mL or more and 3,000 µg/mL or less.

12. The method of producing a hair follicle germ according to claim 1, wherein a concentration of the (b) type IV collagen in the first culture solution is 1 µg/ml or more.

13. The method of producing a hair follicle germ according to claim 12, wherein a concentration of the (b) type IV collagen in the first culture solution is 1 µg/mL or more and 1,000 µg/mL or less.

14. The method of producing a hair follicle germ according to claim 1, wherein the first culture solution comprises (a) laminin and entactin and (b) type IV collagen.

15. The method of producing a hair follicle germ according to claim 1, wherein the epithelial cells and the mesenchymal cells are inoculated simultaneously.

16. The method of producing a hair follicle germ according to claim 1, wherein the epithelial cells and the mesenchymal cells are inoculated serially.

17. The method of producing a hair follicle germ according to claim 1, wherein the mesenchymal cells are inoculated first and subsequently the epithelial cells are inoculated.

18. The method of producing a hair follicle germ according to claim 1, wherein the epithelial cells and the mesenchymal cells are inoculated in the culture solution in which the (a) and/or the (b) is dispersed.

19. The method of producing a hair follicle germ according to claim 1, wherein the epithelial cells and the mesenchymal cells are inoculated in the culture solution in which the (a) and/or the (b) is not dispersed.

* * * * *